US012796975B2

(12) United States Patent
Wederhorn et al.

(10) Patent No.: US 12,796,975 B2
(45) Date of Patent: Nov. 17, 2026

(54) OXYGEN SATURATION CALIBRATION

(71) Applicant: Oura Health Oy, Oulu (FI)

(72) Inventors: Roosa Annikki Wederhorn, Espoo (FI); Ronny Li, San Francisco, CA (US); Olli Petteri Heikkinen, Oulu (FI); Tom Goff, Mountain View, CA (US); Shyamal Patel, San Francisco, CA (US)

(73) Assignee: Oura Health Oy, Oulu (FI)

( * ) Notice: Subject to any disclaimer, the term of this patent is extended or adjusted under 35 U.S.C. 154(b) by 594 days.

(21) Appl. No.: 18/332,368

(22) Filed: Jun. 9, 2023

(65) Prior Publication Data

US 2023/0397852 A1 Dec. 14, 2023

Related U.S. Application Data

(60) Provisional application No. 63/351,219, filed on Jun. 10, 2022.

(51) Int. Cl.
*A61B 5/1455* (2006.01)

(52) U.S. Cl.
CPC .. *A61B 5/14551* (2013.01); *A61B 2560/0238* (2013.01)

(58) Field of Classification Search
CPC . A61B 5/0205; A61B 5/0022; A61B 5/02055; A61B 5/022; A61B 5/0053; A61B 5/1455; A61B 5/14551; A61B 5/14552; A61B 5/1495; A61B 5/02438; A61B 5/6826; A61B 2560/0223; A61B 2560/0238
See application file for complete search history.

(56) References Cited

U.S. PATENT DOCUMENTS

| | | | | |
|---|---|---|---|---|
| 5,111,817 A * | 5/1992 | Clark | A61B 5/14551 | 600/323 |
| 5,218,962 A * | 6/1993 | Mannheimer | A61B 5/14542 | 356/41 |
| 5,782,756 A * | 7/1998 | Mannheimer | A61B 5/14542 | 600/323 |
| 2007/0078316 A1* | 4/2007 | Hoarau | A61B 5/14552 | 600/323 |
| 2008/0071155 A1* | 3/2008 | Kiani | A61B 5/14551 | 600/324 |
| 2014/0275831 A1* | 9/2014 | Osorio | A61B 5/4094 | 600/323 |
| 2015/0150513 A1* | 6/2015 | Kobayashi | A61B 5/14552 | 600/324 |
| 2019/0380655 A1* | 12/2019 | LeBoeuf | A61B 5/02055 | |

* cited by examiner

*Primary Examiner* — Chu Chuan Liu
(74) *Attorney, Agent, or Firm* — ArentFox Schiff LLP

(57) ABSTRACT

Methods, systems, and devices for wearing detection are described. A wearable device may perform a measure of oxygen saturation (e.g., blood oxygen saturation (SpO2)) in a first series of measurements and a second series of measurements at a first locality of an anatomical feature of the user and a second locality of the anatomical feature of the user, respectively. The wearable device may send the first series of measurements and the second series of measurements to a user device of the user. The user device may determine an oxygen saturation calibration by comparing the first and second series of measurements. The user device may calibrate the second series of measurements according to the oxygen saturation calibration.

14 Claims, 17 Drawing Sheets

OXYGEN SATURATION CALIBRATION

CROSS REFERENCE

The present application for patent claims the benefit of U.S. Provisional Patent Application No. 63/351,219 by Wederhorn et al., entitled "OXYGEN SATURATION CALIBRATION," filed Jun. 10, 2022, assigned to the assignee hereof and expressly incorporated by reference herein.

FIELD OF TECHNOLOGY

The following relates to wearable devices and data processing, including oxygen saturation calibration.

BACKGROUND

Some wearable devices may be configured to collect physiological data from users, including temperature data, heart rate data, and the like. However, poor contact between a user's skin and one or more sensors of a wearable device may result in inaccurate measurements.

DETAILED DESCRIPTION

Figure 1:
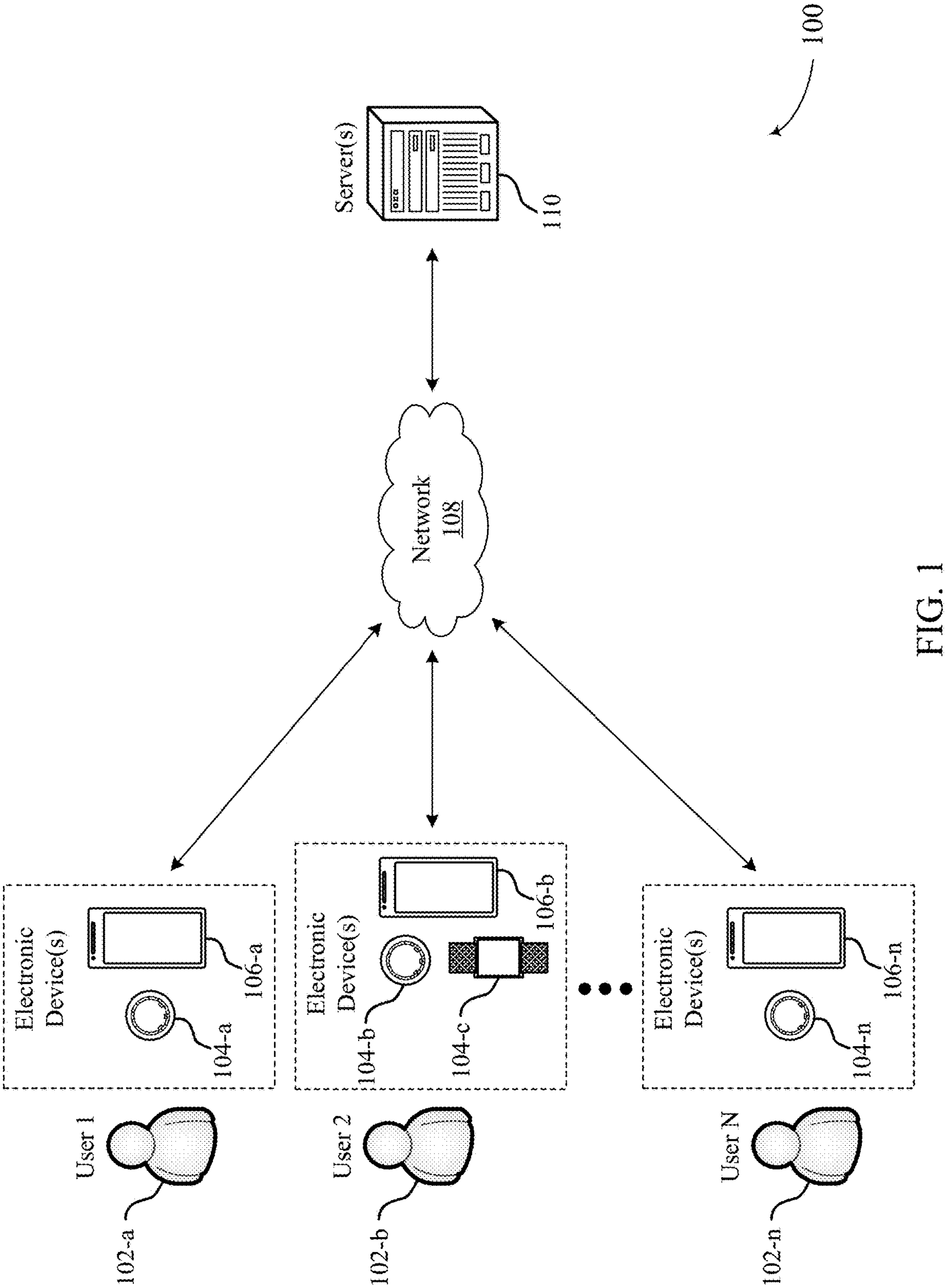
FIG. 1 illustrates an example of a system that supports oxygen saturation calibration in accordance with aspects of the present disclosure.

Some wearable devices may be configured to collect data from users associated with movement and other activities. For example, some wearable devices may be configured to continuously acquire physiological data associated with a user including temperature data, heart rate data, blood oxygen level (SpO2) data, and the like. In order to efficiently and accurately track physiological data, a wearable device may be configured to collect data continuously while the user wears the device. However, in some cases, there may be situations that impact the accuracy of the physiological data collected by the wearable device. For example, there may be a gap between the skin of a user and a wearable device. If the wearable device is a ring, pressure on the ring may create an air gap between the other side of the ring and the skin of the user due to a finger of the user being depressed against the ring. In some other examples, if the wearable device is worn on a wrist of a user, pressure on the device may create an air gap between the opposite side of the device and the skin of the user due to a wrist of the user being depressed against the wearable device. Additionally, or alternatively, the wearable device may be relatively large for a user, which may create gaps between the wearable device and the skin of the user (e.g., ill-fitting ring). The gap may align with one or more sensors of the wearable device, such as one or more light emitting diodes (LEDs), which may create new optical interfaces between the skin of the user and the sensors. Similarly, the wearable device may shift position on the user or may shift orientation on the user. For example, if the wearable device is on a finger of a user, the wearable device may slide from a base of the finger to a tip of the finger or may rotate so the sensors move from the palm of the finger to the back of the finger. The shift in position or orientation may cause new optical interfaces.

The new optical interfaces may behave differently as compared to cases where there is good skin contact between the skin of the user and the sensors in positions or orientations (e.g., may change a critical angle due to reflections, reduce perfusion index due to internal stray light, cause variations in distribution of light, and the like). In some examples, contaminants such as dirt and liquids may be positioned between the wearable device and the finger, which may further distort one or more light wavelengths emitted from the LEDs. The variation in optical interface and wavelength may cause inaccurate readings from the sensors, such as inaccurate SpO2 readings. In some cases, the wearable device may adjust a power of the sensors, such as increasing the brightness of an LED, to account for the variation in readings, which may increase power consumption at the wearable device. Taken together, these issues with wearable devices may result in inaccurate physiological data readings, which may lead to a distorted summary of the user's overall health, as well as increased power consumption and decreased battery life.

Accordingly, techniques described herein are directed to systems and methods for calibrating a wearable device based on a position and orientation of the wearable device on the user. More specifically, techniques described herein are directed to the use of multiple measurements at various positions and applying various pressures to the wearable device to calibrate an SpO2 value. By determining a position and orientation of the wearable device on a user, as well as determining whether there is sufficient skin contact with sensors of a wearable device, techniques described herein may lead to more accurate physiological data measurements, such as SpO2 measurements, and may decrease a power consumption at the wearable device, which may lead to longer battery life.

Aspects of the disclosure are initially described in the context of systems supporting physiological data collection from users via wearable devices. Additional aspects of the disclosure are described in the context of wearable user device diagrams and an example GUI. Aspects of the disclosure are further illustrated by and described with reference to apparatus diagrams, system diagrams, and flow-charts that relate to oxygen saturation calibration.

FIG. 1 illustrates an example of a system 100 that supports oxygen saturation calibration in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time during which the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for calibrating a wearable device 104 for one or more oxygen saturation (e.g., SpO2) measurements from a user 102. Specifically, techniques described herein support taking measurements at varying locations, or localities, of anatomical features of the user 102. For example, the wearable device 104 may perform a series of measurements to use as base SpO2 values, where the series of measurements may be at different orientations of the wearable device 104 (e.g., as the wearable device 104 rotates) or as different forces are applied to the wearable device 104. The user 102 may position the wearable device 104 at a location where the SpO2 measurements may be relatively accurate, such as at a tip of a finger if the wearable device 104 is a ring, which is described in further detail with respect to FIG. 4. Once the wearable device 104 performs the series of SpO2 measurements, the wearable device 104 may send the SpO2 measurement values to a user device 106 of the user 102. The wearable device 104 may continue to perform additional SpO2 measurements and report these additional measurements to the user device 106, which is described in further detail with respect to FIG. 4. The user device 106 may compare the additional SpO2 measurements to the initial series of SpO2 measurements to calculate an SpO2 calibration. In some cases, the user device 106 may display the calibrated SpO2 to the user 102 via a GUI at the user device 106.

It should be appreciated by a person skilled in the art that one or more aspects of the disclosure may be implemented in a system 100 to additionally, or alternatively, solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
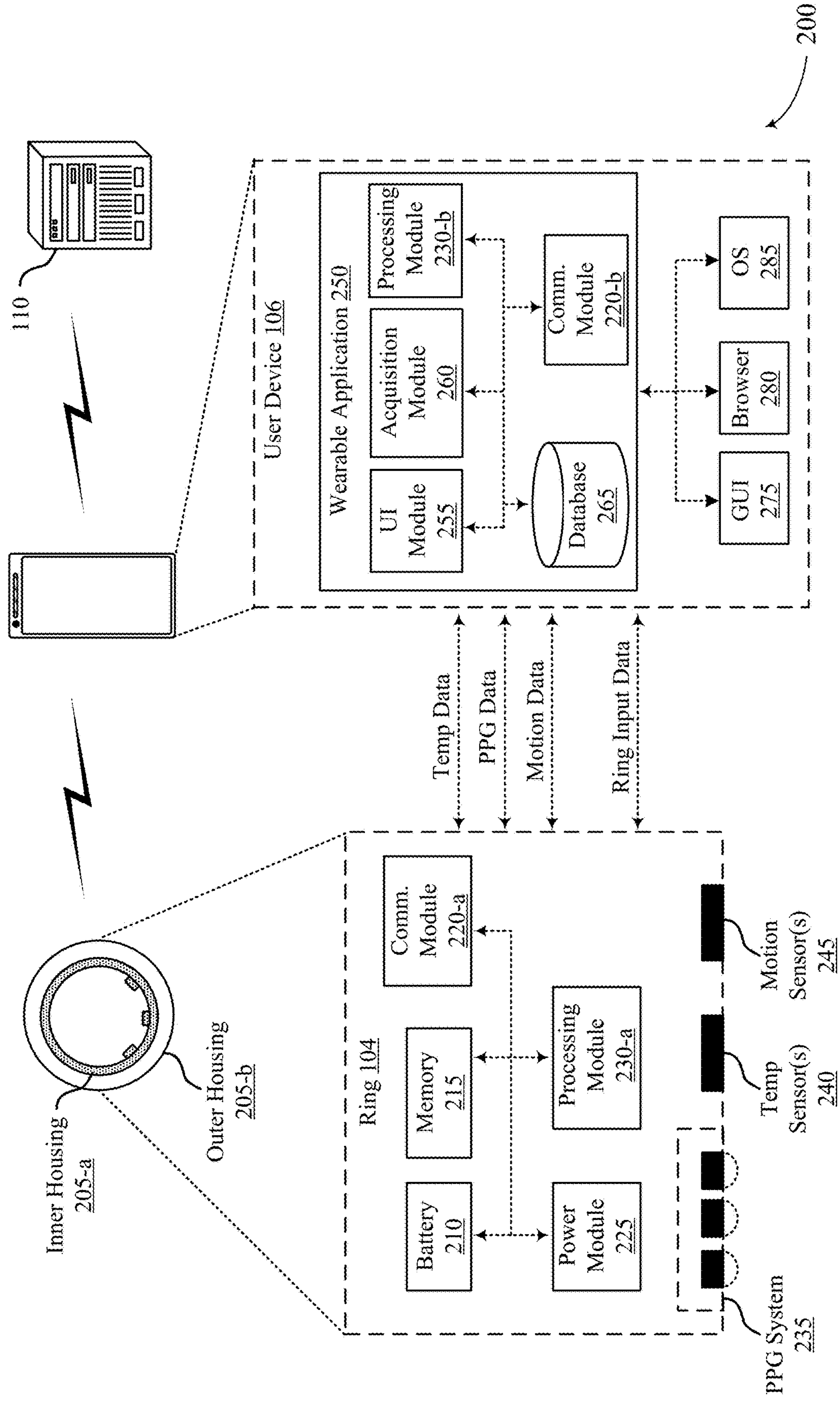
FIG. 2 illustrates an example of a system that supports oxygen saturation calibration in accordance with aspects of the present disclosure.

FIG. 2 illustrates an example of a system 200 that supports oxygen saturation calibration in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components.

For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*a*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBls. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for calibrating one or more measurements of a wearable device 104 using multiple measurements from localities of an anatomical feature of a user. The anatomical feature may be a human finger or any other human body part, such as an appendage, a neck, a head, a chest, or the like. In some cases, the wearable device 104 may record temperature measurements, PPG measurements, motion measurements, pressure measurements, SpO2 measurements, or any combination thereof using the temperature sensors 240, the PPG system 235, and any other sensors of the wearable device 104. In some examples, the PPG measurements may include two separate optical channel PPG measurements to obtain an SpO2 measurement. A user device 106, or another device with access to the data, may use the temperature data, the PPG data, the motion data, the pressure data, or any combination thereof to calibrate one or more sensors of the wearable device 104. For example, the one or more sensors may be calibrated to adjust for variability in user-to-user measurements or measurements at different positions or orientations of the anatomical feature relative to the wearable device 104.

Figure 3A:
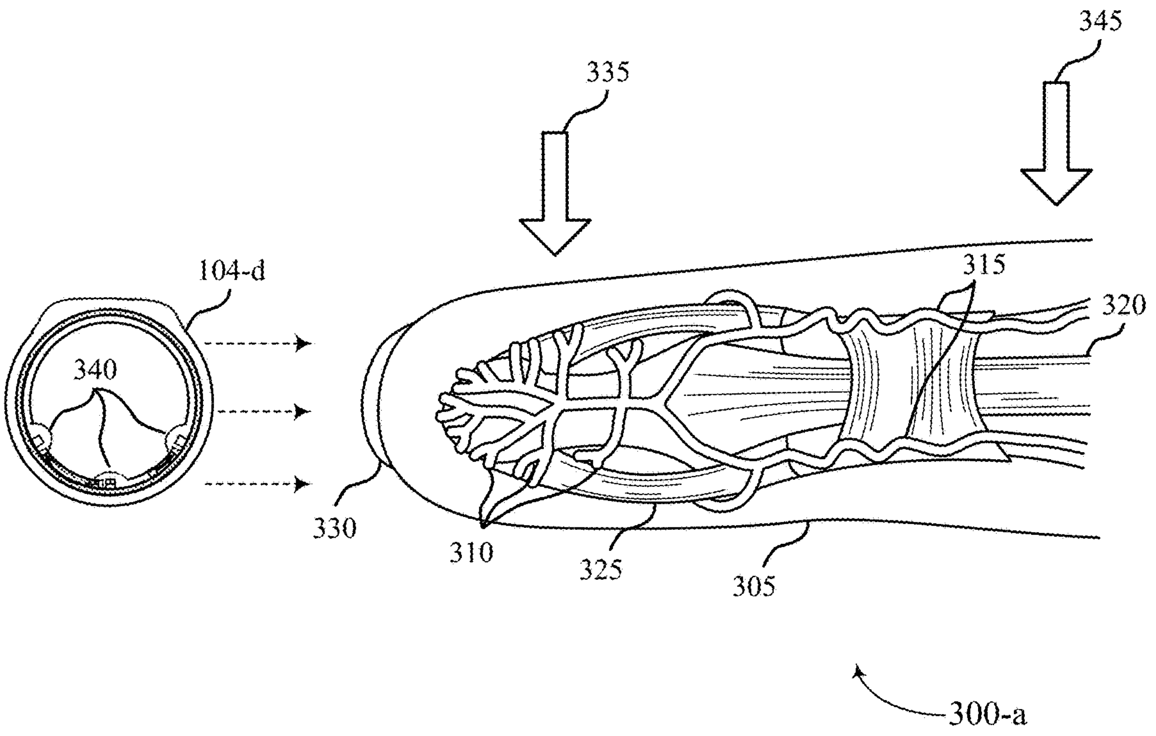
FIGS. 3A, 3B, and 4 illustrate examples of wearable device diagrams that support oxygen saturation calibration in accordance with aspects of the present disclosure.
Figure 3B:
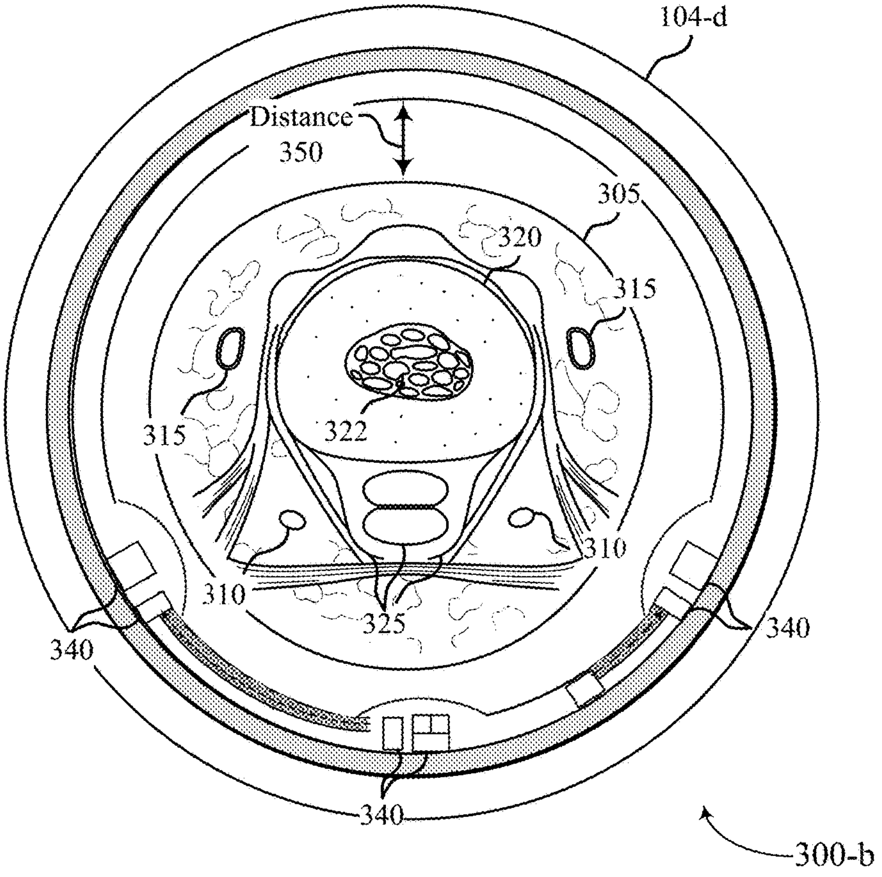

FIGS. 3A and 3B illustrate examples of a wearable device diagram 300-*a* and a wearable device diagram 300-*b* that support oxygen saturation calibration in accordance with aspects of the present disclosure. The wearable device diagram 300-*a* and the wearable device diagram 300-*b* may implement, or be implemented by, aspects of the system 100, system 200, or both. For example, the wearable device diagram 300-*a* and the wearable device diagram 300-*b* may illustrate examples of coupling a wearable device 104-*d* to an anatomical feature 305 of a user for calibration, where the wearable device 104-*d* may be an example of a wearable device 104 as described with reference to FIGS. 1 and 2. Specifically, the wearable device diagram 300-*a* and the wearable device diagram 300-*b* may illustrate contents and functionality of an anatomical feature 305 at different localities. Although the anatomical feature 305 is illustrated as a finger in FIGS. 3A and 3B, the anatomical feature 305 may represent any human body part for any example of a wearable device (e.g., a wrist for a watch, a neck for a necklace, and the like).

In some cases, the anatomical feature 305 may include one or more elements, such as capillaries 310 and arteries 315 (e.g., veins of a user) through which blood may flow. The capillaries 310 and the arteries 315 may have muscle tissue in the vein walls, which may impact the amount of light that may penetrate the capillaries 310 and the arteries 315. For example, the arteries 315 may have thicker muscle tissue than the arteries 315, such that the light may penetrate the walls of the capillaries 310 more effectively than the walls of the arteries 315. Additionally, or alternatively, the capillaries 310 may be a shorter distance below the surface of the anatomical feature 305 than the arteries 315, such that one or more wearable device sensors 340 may collect more accurate measurements from the capillaries 310. For example, the arteries 315, which may represent human arteries, may be located 3 millimeters (mm) below the surface of the anatomical feature 305. The arteries 315 may have a threshold diameter, such as 1.2 mm. The capillaries 310, which may be representative of human capillaries, may be closer to the surface of the anatomical feature 305 than the arteries 315 (e.g., 10 microns below the surface). The capillaries 310 may branch out from the arteries 315 to create layers of human veins. Thus, in some examples, a wearable device sensor 340 may test different penetration depths to collect measurements (e.g., SpO2 measurements).

In addition to the capillaries 310 and the arteries 315, the anatomical feature 305 may include one or more of human bone 320, human ligaments 325, human nails 330, human muscle, or any other aspects of a human appendage (e.g., finger). For example, as illustrated in FIGS. 3A and 3B, the anatomical feature 305 may include one or more human bones 320 with bone marrow 322, human ligaments 325 (e.g., human tissue), human nails 330, or any combination thereof, which may have optical, thermal, or mechanical properties that impact a measurement from one or more wearable device sensor 340 of the wearable device 104-*d*. That is, the elements may have different light transmission and scatter and absorption properties, such as scatter and absorption properties related to a signal from pulsating blood-containing tissue in a PPG measurement (e.g., SpO2 measurement). In some examples, a set of wavelengths may penetrate the surface of the anatomical feature 305, such as 940 nanometers (nm) for human skin. The wearable device 104-*d* may perform one or more measurements, such as heart rate and oxygen saturation (e.g., SpO2) measurements.

In some examples, one or more users, such as users 102 as described with reference to FIG. 1, may use a wearable device 104-*d* to collect one or more health metrics, such as heart rate, body temperature, oxygen saturation, movement, etc. Each user may have unique attributes, such that an average health metric for each user may vary. For example, a user may have a different average heart rate, body temperature, or the like when compared with another user. Similarly, different localities of the anatomical feature 305 of a user may have unique attributes (e.g., due to the variation in elements at the different localities). Due to the variations, it may be difficult to use the data from each user and different localities of a user to detect health related trends. For example, if a user has a naturally high or low heart rate, the wearable device may misdiagnose the high heart rate as a trend towards an illness and may not detect a high heart rate trend towards an illness for the low heart rate user, instead detecting a heart rate within a "normal" range. Similarly, there may be variation between SpO2 measurements from different localities on the user, which may cause relatively high or low readings that may be inaccurate.

Thus, as described herein, a wearable device 104-*d* may be calibrated using different localities of an anatomical feature 305 of a user, as illustrated in FIGS. 3A and 3B. In some cases, the anatomical feature 305 may be a human wrist, ankle, arm, leg, finger, or any other appendage to calibrate a wearable device 104-*d*, such as a watch or wrist band, an ankle band, an arm band, a leg band, or a ring, respectively. FIG. 3A shows a top view of the anatomical feature 305, while FIG. 3B shows a cross section of the anatomical feature 305. In some cases, the anatomical feature 305 may provide for a user to collect information that may stabilize measurements (e.g., oxygen saturation measurements, or SpO2 measurements) by the hardware of the wearable device 104-*d*. The anatomical feature 305 may vary in elements based on locality, such that the wearable device 104-*d* may collect relatively accurate measurements at an initial locality 335 of the anatomical feature 305 due to the composition of the anatomical feature 305. For example, the initial locality 335 may include one or more capillaries 310 that may be relatively close to the surface of the anatomical feature 305 and may have relatively thin walls. Thus, the light from one or more wearable device sensors 340 of the wearable device 104-*d*, such as sensors of a PPG system as described with reference to FIG. 2, may penetrate the capillaries 310 for a relatively accurate measurement (e.g., blood oxygen measurement, or SpO2 measurement).

The wearable device 104-*d* may collect additional measurements at a secondary locality 345, and report the initial measurements and the additional measurements to a user device. The anatomical feature 305 may have a different composition at the secondary locality 345. For example, the anatomical feature 305 at the secondary locality 345 may include one or more arteries 315, which may have relatively thick walls and may be located deeper within the anatomical feature. The thicker walls and human ligaments 325, or other tissue, may block or otherwise disrupt the light from the one or more wearable device sensors 340 of the wearable device 104-*d*, such that the light may not sufficiently penetrate the arteries 315 for an accurate measurement. Thus, the user device may compare the initial measurements and the additional measurements to acquire a calibration value for the additional measurements. The user device may configure the value of the additional measurements according to the results.

In some cases, one or more wearable devices, such as the wearable device 104-*d*, may couple with the anatomical feature 305 at the initial locality 335, the secondary locality 345, or both. Wearable device sensors 340, which may be referred to as sensors, may be located on the inside of the wearable device 104-*d*. In some examples, the wearable device sensors 340 may include LEDs, pressure sensors, thermal sensors, or the like, for detecting optical, thermal, and mechanical properties. A user may place the wearable device 104-*d* over the anatomical feature 305 at the initial locality 335 or the secondary locality 345 for calibration of the measurements from the one or more wearable device sensors 340 (e.g., based on instructions from a user device), which is described in further detail with respect to FIG. 4. For example, a user device may instruct the user to place the wearable device 104-*d* at the initial locality 335 of the anatomical feature 305 for the initial measurements. Subsequently, the user device may instruct the user to place the wearable device 104-*d* at the secondary locality 345 for the additional measurements. In some examples, FIG. 3B may illustrate an example of a cross section at the secondary locality 345. In some cases, the user may apply a set of forces or change the orientation of the wearable device 104-*d* (e.g., by rotating the wearable device 104-*d*). For example, the user may apply a force to maximize a distance 350 between the top of the anatomical feature 305 and the top of the wearable device 104-*d*, or in other words, to minimize a distance between the one or more wearable device sensors 340 and the skin of a user. In some examples, full contact of the wearable device sensors 340 with the skin of the user may reduce variation and improve accuracy of the measurements.

The wearable device sensors 340 may measure properties of the blood flowing through the capillaries 310 and the arteries 315 of the anatomical feature 305 (e.g., based on a perfusion index) that may be interpreted to indicate vital signs of the user, such as heart rate, oxygen saturation level (e.g., SpO2), body temperature, or the like. The wearable device sensors 340 may also measure fluid properties correlating to other physiological parameters other than vital signs. The wearable device sensors 340 may include LED and photodetector sensor pairs which may measure internal stray light within the anatomical feature 305 or other properties of the anatomical feature 305. In reference to FIG. 2, in some examples, the LED and photodetector sensors may measure PPG signal data, such as pulse waveforms and data calculated based on the pulse waveforms (e.g., heart rate values, IBI values, HRV values, and respiratory rate values). In some other examples, the LED and photodetector sensors may measure oxygen saturation levels, or an SpO2 value.

Figure 4:
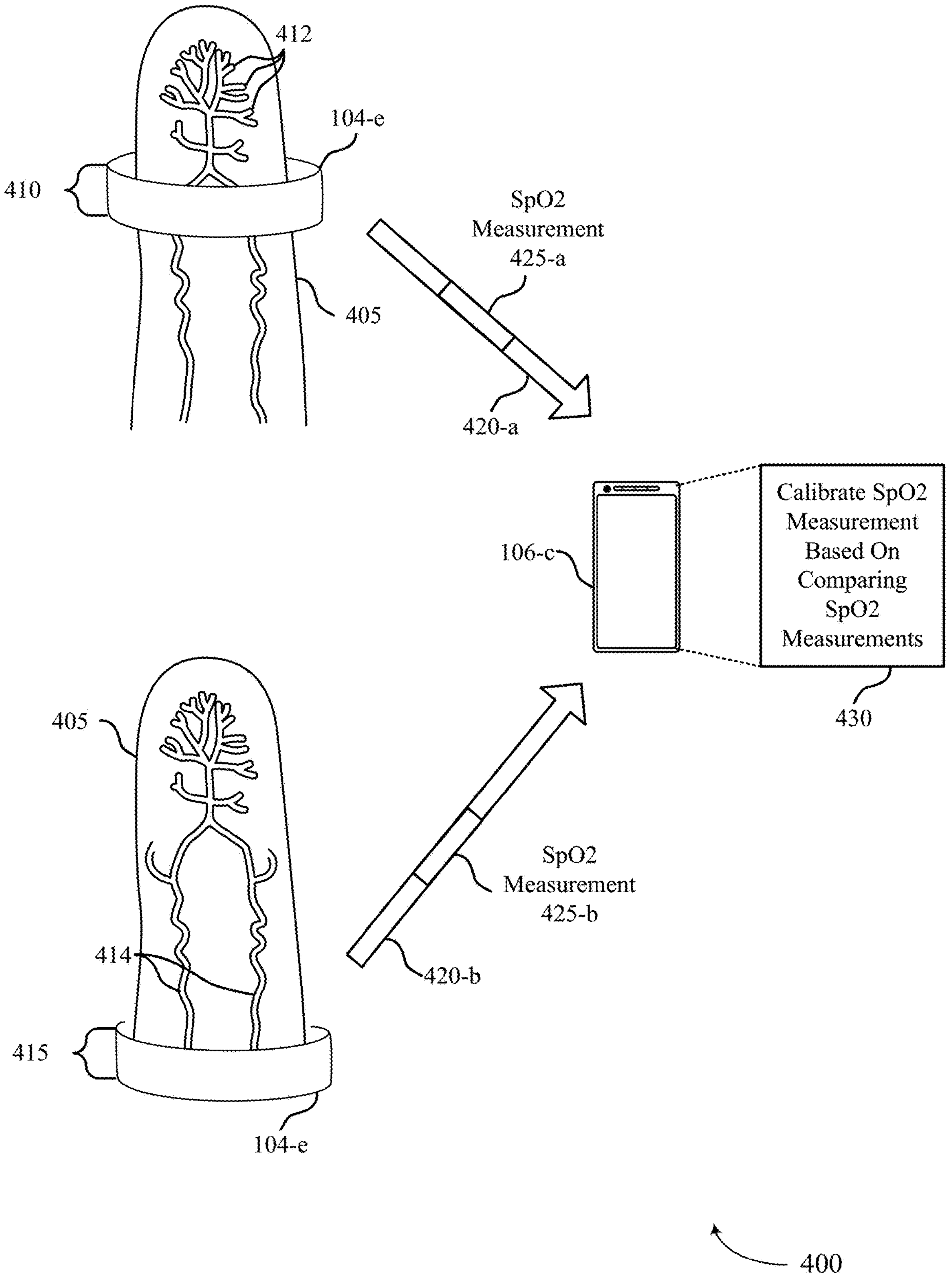

FIG. 4 illustrates an example of a wearable device diagram 400 that supports oxygen saturation calibration in accordance with aspects of the present disclosure. The wearable device diagram 400 may illustrate the calibration of measurements from a wearable device 104-*e* using a user device 106-*c*, which may be examples of wearable devices 104 and user devices 106, respectively, as described with reference to FIGS. 1, 2, 3A, and 3B. A user may place the wearable device 104-*e* at different localities of an anatomical feature 405 (e.g., a finger) for measurements and sensor calibration. Although the wearable devices are illustrated as rings in FIG. 4, they may be any example of a wearable device (e.g., a watch, a necklace, and the like).

In some cases, a user of the wearable device 104-*e* may position the wearable device 104-*e* at an initial locality 410 of the anatomical feature 405 for an initial set of measurements. The measurements may include an oxygen saturation measurement, which may provide an SpO2 value. For example, the user device 106-*c* may instruct the user to place the wearable device 104-*e* at the initial locality 410 based on messaging using a GUI, which is described in further detail with respect to FIG. 5. After positioning the wearable device 104-*e* at the initial locality 410, the user may move the wearable device 104-*e* to a secondary locality 415 (e.g., based on additional messaging from the user device 106-*c*).

In some examples, if the anatomical feature 405 is a finger, the initial locality 410 may be a tip of the finger and the secondary locality 415 may be a knuckle, a base of the finger, or any other area on the finger besides the tip of the finger. The fingertip at the initial locality 410 may have multiple capillaries 412 where tissue may be similar across the fingertip (e.g., predictable for sensor measurements). At the secondary locality, the finger may have larger arteries 414 with different tissue layers than in the capillaries 412. The muscles in the walls of the artery may impact the signal from one or more sensors of the wearable device 104-*e*. Thus, overall, the signals from the one or more sensors in the fingertip at the initial locality 410 may be relatively stronger and more stable than the signals at the secondary locality 415 away from the fingertip.

In some examples, the user may use a same wearable device 104-*e* and take initial measurements at the initial locality 410, then move the wearable device 104-*e* and take additional measurements at the secondary locality 415. In some other examples, the user may have an additional wearable device, such that the user may take the initial measurements at the initial locality 410, while leaving the wearable device 104-*e* at the secondary locality 415 for the additional measurements. The wearable device 104-*e*, the additional wearable device, or both may report the initial measurements and the additional measurements to the user device 106-*c*, where the initial measurements and the additional measurements may include SpO2 measurements. For example, the wearable device 104-*e* may transmit signaling (e.g., wireless signaling) via a communication link 420-*a* to the user device 106-*c*, the signaling including an SpO2 measurement 425-*a* from the initial measurements at the initial locality 410. The wearable device 104-*e* may transmit additional signaling via a communication link 420-*b* to the user device 106-*c*, the signaling including an SpO2 measurement 425-*b* from the additional measurements at the secondary locality 415.

In some examples, such as due to the variation in wall thickness between arteries 414 at the secondary locality 415 and the capillaries 412 at the initial locality 410, the SpO2 measurement 425-*b* may drift in value when compared to the SpO2 measurement 425-*a*. Thus, at 430, the user device 106-*c* may calibrate the SpO2 measurement 425-*b* based on comparing the SpO2 measurement 425-*a* and the SpO2 measurement 425-*b*. The comparison may provide an SpO2 calibration to the user device 106-*c*. The user device 106-*c* may shift a floor of the SpO2 measurement 425-*b* at the secondary locality 415 (e.g., a finger base measurement) by the SpO2 measurement 425-*a* at the initial locality 410 (e.g., a fingertip measurement). In some cases, the oxygen saturation calibration may be based on a pulse rate of the user, a signal interference value for the SpO2 measurement 425-*b*, an environmental factor, accelerometer (e.g., movement) data, pressure data, or any combination thereof.

In some cases, the user device 106-*c* may configure a periodicity (e.g., a threshold duration between measurements) for the wearable device 104-*e* to perform one or more measurements at the initial locality 410, which may be different from a periodicity for the wearable device 104-*e* to perform one or more measurements at the secondary locality 415. For example, the user device 106-*c* may indicate to a user to perform a measurement procedure at the initial locality 410 (e.g., the fingertip) every 24 hours, while the measurements at the secondary locality 415 occur by the minute. The measurement procedure may include applying a series of forces, a series of orientations, or both to the wearable device 104-*e*. For example, the user may apply a force in each direction (left, right, top, bottom, etc.) to the wearable device 104-*e* based on a message at the user device 106-*c*. Additionally, or alternatively, the user may rotate the wearable device 104-*e* to a series of orientations for the sensors based on a message at the user device 106-*c*. In some examples, the user device 106-*c* may update an SpO2 calibration value (e.g., oxygen saturation calibration) periodically.

In some examples, the initial locality 410 may be on a different human body part than the secondary locality 415 (e.g., two different anatomical features 405). For example, if the wearable device 104-*e* is a necklace, the initial locality 410 may be a wrist, while the secondary locality 415 may be a neck of the user, such as if the wrist provides more accurate measurements for SpO2 calibration than the neck. In some other examples, the initial locality 410 may be on the same human body part (e.g., a single anatomical feature 405) as the secondary locality 415, as illustrated in FIG. 4. For example, the human body part may be a finger, and the initial locality 410 may be the tip of the finger, and the secondary locality 415 may be at the base of the finger.

In some examples, the user device 106-*c* may generate a data structure (e.g., a database of values) based on comparing different SpO2 measurements. The data structure may map SpO2 measurements to a position of the wearable device 104-*e*, an orientation of the wearable device 104-*e*, a pressure applied to the wearable device 104-*e*, or any combination thereof. The user device 106-*c* may use the generated data structure to come up with a calibration value for future SpO2 measurements (e.g., by looking up the value rather than comparing measurements to obtain the value). Generating the data structure may reduce a numerical quantity of times the user performs the calibration procedure, due to recording different calibration use cases in the data structure for lookup.

In some examples, the periodicity of the calibration at the user device 106-*c* may be based on a rate of change of pressure between the wearable device 104-*e* and the anatomical feature 405. The rate of change of pressure may be based on an activity level of the user, a material of the wearable device 104-*e*, or any other factor. For example, if the wearable device 104-*e* is a rigid body, rather than a malleable body, the change in SpO2 level between the SpO2 measurement 425-*a* and the SpO2 measurement 425-*b*, and consequently the rate of change of the pressure, may be relatively large. The user device 106-*c* may reduce a periodicity of the calibrations for a wearable device 104-*e* with a material that expands and contracts with the natural process of the anatomical feature 405. For example, if a finger swells, the wearable device 104-*e* may stretch, such that the sensors maintain a threshold distance with the skin. Similarly, if the finger contracts, the wearable device 104-*e* may match the contraction, such that the sensors maintain the threshold distance with the skin. Additionally, or alternatively, the sensors of the wearable device 104-*e* may be connected to a spring, such that the sensors may move with the expansion and contraction of the anatomical feature 405.

In some examples, the pulsation of the arteries 414 may add a motion element to the measurements from the wearable device 104-*e*. The motion element may cause variations between measurements at the initial locality 410 and the secondary locality 415, or between measurements at the secondary locality 415. In some cases, the motion element may change based on an orientation of the wearable device 104-*e*. Thus, the user device 106-*c* may indicate for the user to perform measurements at a series of rotations (e.g., a rotation sequence) when the wearable device 104-*e* is at the initial locality 410, the secondary locality 415, or both. The user device 106-*c* may use the measurements from the series of rotations to filter the SpO2 measurements 425-*b* at 430. Additionally, or alternatively, the user device 106-*c* may filter out one or more inaccurate measurements using an accelerometer, temperature sensors, or both (e.g., from a temperature map) to determine a rotation of the wearable device 104-*e*.

In some cases, the wearable device 104-*e* may use a higher sampling phase at the initial locality 410, or when applying the series of forces, the series of orientations, or both (e.g., during a calibration phase). Additionally, or alternatively, the measurements may be intermittent, such that the wearable device 104-*e* may perform a series of measurements, wait for a period, then perform an additional series of measurements, where the SpO2 measurement 425-*a* includes both series of measurements. In some examples, the user device 106-*c* may determine one or more of the sensors (e.g., photodetectors) are reporting more accurate measurements than one or more other sensors. For example, the user device 106-*c* may select one or more quality metrics for choosing which photodetectors are stable. The user device 106-*c* may use the SpO2 measurements from the stable photodetectors for the calibration procedure.

In some cases, the user device 106-*c* may analyze the SpO2 measurement 425-*a* and the SpO2 measurement 425-*b* to determine whether the wearable device 104-*e* has lost skin contact with the anatomical feature 405. For example, the user device 106-*c* may use a stray light metric, a temperature metric, inertia related to accelerometer data, or any combination thereof reported by the wearable device 104-*e* to determine the wearable device 104-*e* has lost skin contact. If the wearable device 104-*e* has lost skin contact with the anatomical feature 405, the user device 106-*c* may discard the measurements reported for a duration in which the loss of skin contact occurs. In some examples, the user device may determine a force applied to the exterior surface of the wearable device 104-*e*, an orientation of the wearable device 104-*e*, or both based on comparing the SpO2 measurement 425-*b* to the SpO2 measurement 425-*a*.

Figure 5:
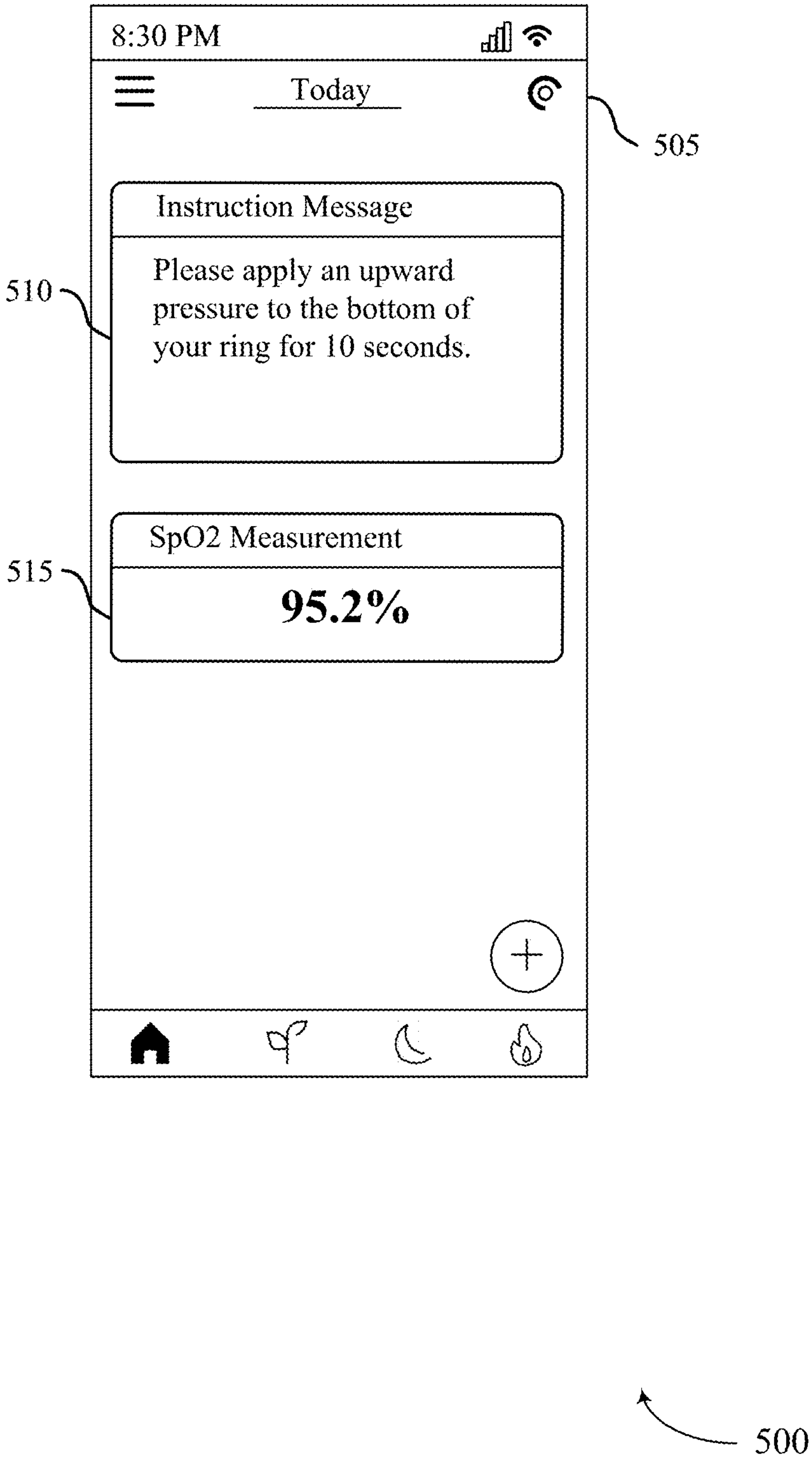
FIG. 5 illustrates an example of a graphical user interface (GUI) that supports oxygen saturation calibration in accordance with aspects of the present disclosure.

FIG. 5 illustrates an example of a GUI 500 that supports oxygen saturation calibration in accordance with aspects of the present disclosure. The GUI 500 may implement, or be implemented by, aspects of the system 100, the system 200, the wearable device diagram 300-*a*, the wearable device diagram 300-*b*, the wearable device diagram 400, or a combination thereof. For example, the GUI 500 may illustrate examples of a user device 505 reporting an oxygen saturation calibration (e.g., SpO2 value) to a user, instructions for calibrating an oxygen saturation at the wearable device, or both, where the user device 505 may be an example of a user device 106 as described with reference to FIG. 1.

In some examples, the user device 505 may indicate one or more instructions in an instruction message 510 to a user via the GUI 500 of the user device 505. The instruction message 510 may indicate for the user to apply a series of forces to the wearable device for a duration (e.g., "Please apply an upward pressure to the bottom of your ring for 10 seconds"). Additionally, or alternatively, the instruction message may indicate for the user to apply a series of rotations to achieve different orientations of the wearable device. While the user is applying the forces, rotations, or both, the wearable device may perform one or more measurements (e.g., SpO2 measurements) to obtain an oxygen saturation. In some examples, the instruction message 510 may also indicate a locality for the user to move the wearable device to for the measurements (e.g., a fingertip). The GUI 500 may display a series of instruction messages, including the instruction message 510, for a calibration procedure. Once the calibration procedure is complete, the GUI 500 may indicate to the user a termination message (e.g., "Calibration complete").

In some cases, the wearable device may detect that a user is not wearing the wearable device and/or may detect a gap between one or more sensors in the inner housing of the wearable device and the skin of a user, as described with respect to FIG. 4. Once the wearable device detects poor skin contact, the wearable device may send an indication of the poor skin contact to the user device 505 of the user. The user device 505 may send the instruction message 510 based on receiving the indication, which may alert the user to perform an action. In some cases, the GUI 500 may prompt the user to acknowledge the instruction message 510, such as by pressing a "confirm" or "dismiss" button. In some examples, the GUI 500 may display an indication of the orientation of the wearable device, an instruction to adjust the orientation of the wearable device, or both. For example, the GUI 500 may display an indication of the orientation of a ring with respect to a finger.

In some cases, the user device 505 may display a calibrated SpO2 value in an SpO2 measurement display 515 (e.g., "95.2%"). The SpO2 value may be calibrated according to the instructions in the instruction message at 510, as described with reference to FIGS. 3A, 3B, and 4. The GUI 500 may display the SpO2 value as a percentage. In some examples, the user may be able to initiate a measurement calibration for oxygen saturation based on pressing a calibration button displayed on the GUI 500. For example, a user may determine an SpO2 measurement display 515 is incorrect, and may initiate a calibration of the wearable device accordingly.

Figure 6:
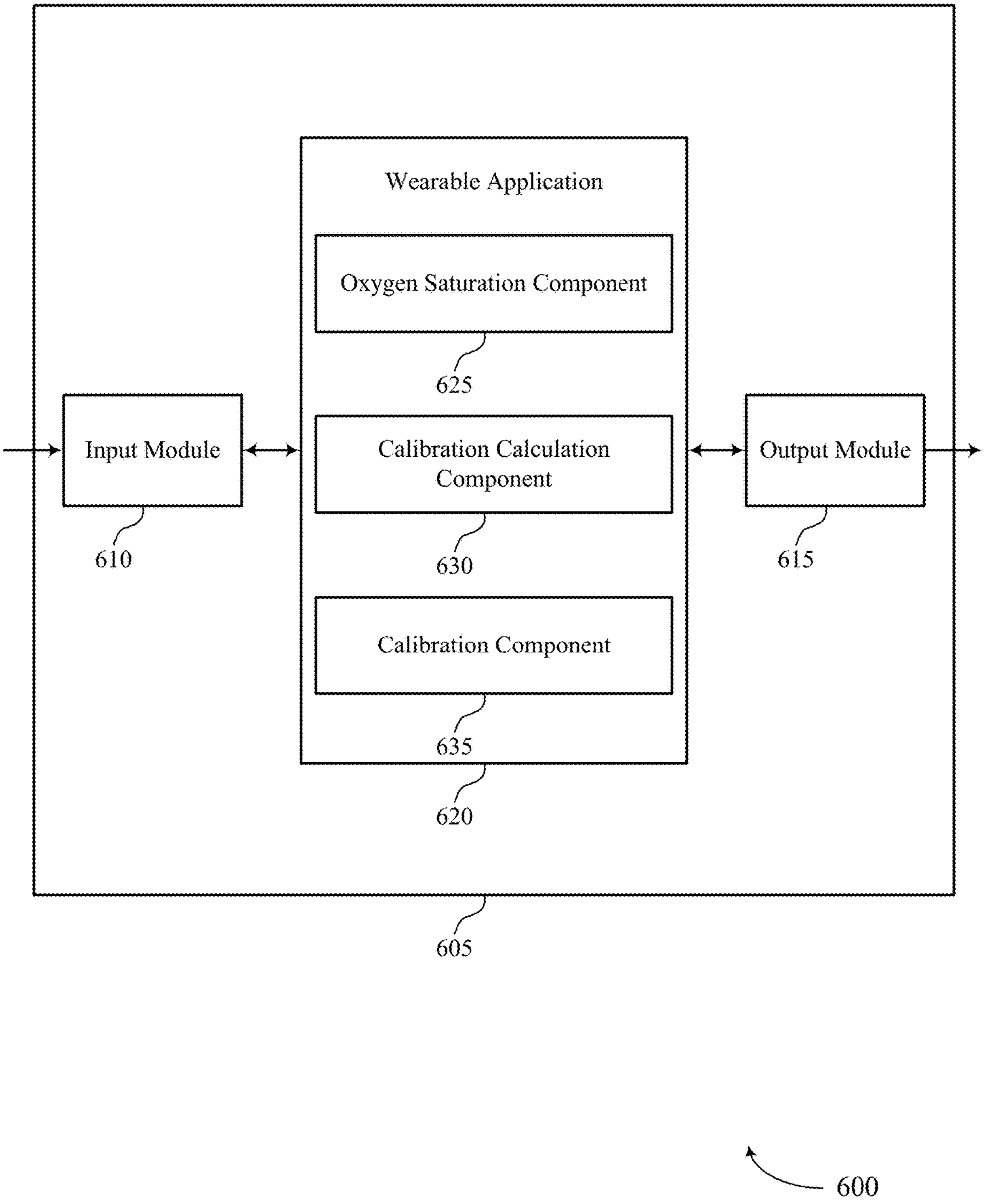
FIG. 6 shows a block diagram of an apparatus that supports oxygen saturation calibration in accordance with aspects of the present disclosure.

FIG. 6 shows a block diagram 600 of a device 605 that supports oxygen saturation calibration in accordance with aspects of the present disclosure. The device 605 may include an input module 610, an output module 615, and a wearable application 620. The device 605 may also include a processor. Each of these components may be in communication with one another (e.g., via one or more buses).

The input module 610 may provide a means for receiving information such as packets, user data, control information, or any combination thereof associated with various information channels (e.g., control channels, data channels, information channels related to illness detection techniques). Information may be passed on to other components of the device 605. The input module 610 may utilize a single antenna or a set of multiple antennas.

The output module 615 may provide a means for transmitting signals generated by other components of the device 605. For example, the output module 615 may transmit information such as packets, user data, control information, or any combination thereof associated with various information channels (e.g., control channels, data channels, information channels related to illness detection techniques). In some examples, the output module 615 may be co-located with the input module 610 in a transceiver module. The output module 615 may utilize a single antenna or a set of multiple antennas.

For example, the wearable application 620 may include an oxygen saturation component 625, a calibration calculation component 630, a calibration component 635, or any combination thereof. In some examples, the wearable application 620, or various components thereof, may be configured to perform various operations (e.g., receiving, monitoring, transmitting) using or otherwise in cooperation with the input module 610, the output module 615, or both. For example, the wearable application 620 may receive information from the input module 610, send information to the output module 615, or be integrated in combination with the input module 610, the output module 615, or both to receive information, transmit information, or perform various other operations as described herein.

The wearable application 620 may support performing calibration of a wearable device in accordance with examples as disclosed herein. The oxygen saturation component 625 may be configured as or otherwise support a means for receiving, from the wearable device, a first measure of oxygen saturation associated with a user based at least in part on a first oxygen saturation measurement, wherein the first oxygen saturation measurement is performed at a first anatomical feature of the user. The oxygen saturation component 625 may be configured as or otherwise support a means for receiving, from the wearable device, a second measure of oxygen saturation associated with the user based at least in part on a second oxygen saturation measurement, wherein the second oxygen saturation measurement is performed at a second anatomical feature of the user. The calibration calculation component 630 may be configured as or otherwise support a means for determining an oxygen saturation calibration based at least in part on comparing the first measure of oxygen saturation and the second measure of oxygen saturation. The calibration component 635 may be configured as or otherwise support a means for calibrating the second measure of oxygen saturation according to the determined oxygen saturation calibration.

Figure 7:
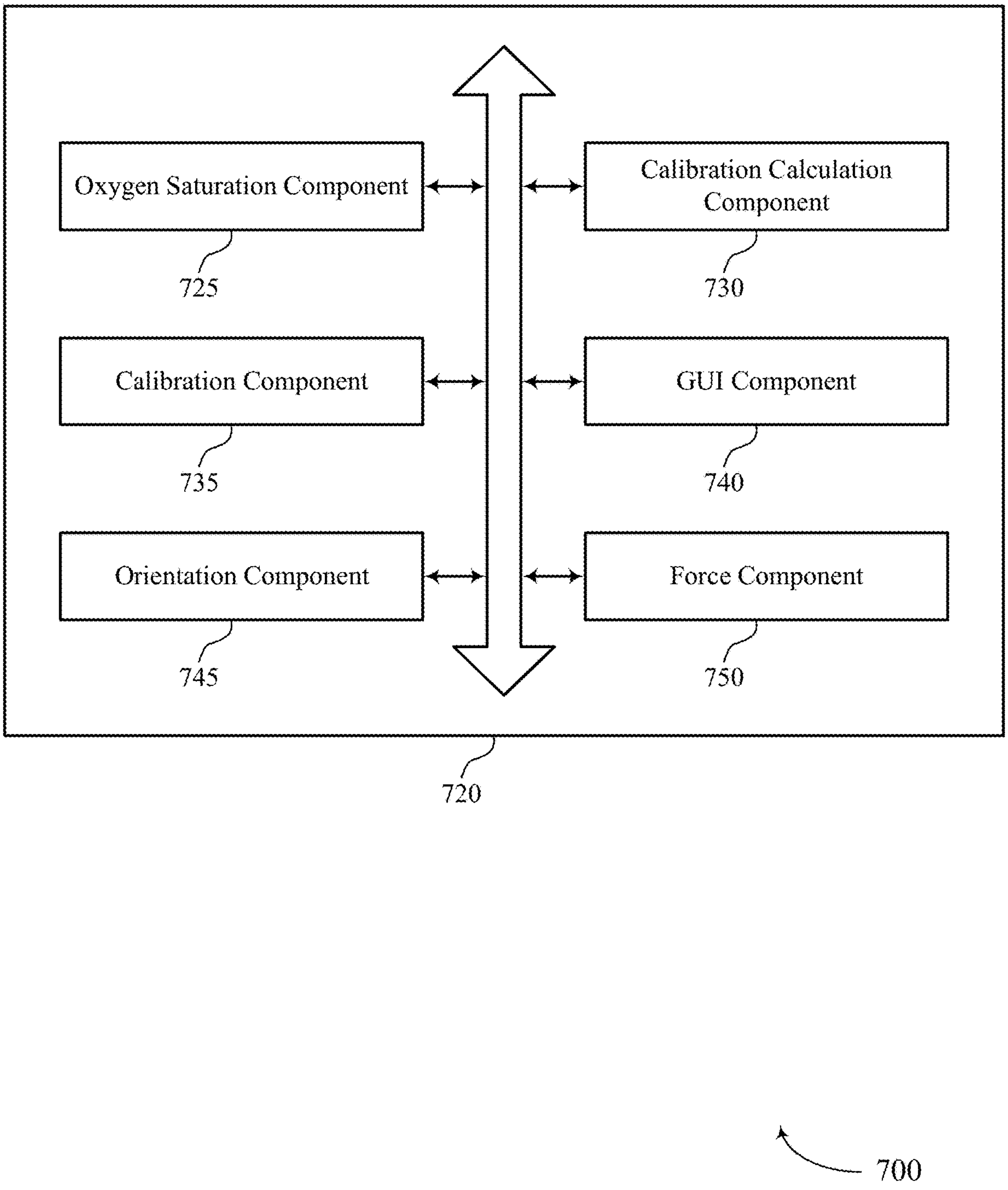
FIG. 7 shows a block diagram of a wearable application that supports oxygen saturation calibration in accordance with aspects of the present disclosure.

FIG. 7 shows a block diagram 700 of a wearable application 720 that supports oxygen saturation calibration in accordance with aspects of the present disclosure. The wearable application 720 may be an example of aspects of a wearable application or a wearable application 620, or both, as described herein. The wearable application 720, or various components thereof, may be an example of means for performing various aspects of oxygen saturation calibration as described herein. For example, the wearable application 720 may include an oxygen saturation component 725, a calibration calculation component 730, a calibration component 735, a GUI component 740, an orientation component 745, a force component 750, or any combination thereof. Each of these components may communicate, directly or indirectly, with one another (e.g., via one or more buses).

The wearable application 720 may support performing calibration of a wearable device in accordance with examples as disclosed herein. The oxygen saturation component 725 may be configured as or otherwise support a means for receiving, from the wearable device, a first measure of oxygen saturation associated with a user based at least in part on a first oxygen saturation measurement, wherein the first oxygen saturation measurement is performed at a first anatomical feature of the user. In some examples, the oxygen saturation component 725 may be configured as or otherwise support a means for receiving, from the wearable device, a second measure of oxygen saturation associated with the user based at least in part on a second oxygen saturation measurement, wherein the second oxygen saturation measurement is performed at a second anatomical feature of the user. The calibration calculation component 730 may be configured as or otherwise support a means for determining an oxygen saturation calibration based at least in part on comparing the first measure of oxygen saturation and the second measure of oxygen saturation. The calibration component 735 may be configured as or otherwise support a means for calibrating the second measure of oxygen saturation according to the determined oxygen saturation calibration. In some examples, the first anatomical feature and the second anatomical feature may be associated with different localities of a same human body part of the user. In some other examples, the first anatomical feature may be associated with a first human body part of the user and the second anatomical feature may be associated with a second human body part of the user.

In some examples, the GUI component 740 may be configured as or otherwise support a means for causing a GUI of a user device to display an indication of the calibrated second measure of oxygen saturation associated with the user. In some examples, determining an orientation of the wearable device based at least in part on the second oxygen saturation measurement, wherein the oxygen saturation calibration is in accordance with the orientation of the wearable device. In some examples, the set of orientations includes a rotation sequence for the wearable device. In some examples, determining a force applied to the exterior surface of the wearable device based at least in part on the second oxygen saturation measurement, wherein the oxygen saturation calibration is in accordance with the force.

In some examples, to support calibrating the second measure of oxygen saturation, the calibration component 735 may be configured as or otherwise support a means for filtering the second oxygen saturation measurement based at least in part on a position of the wearable device, an orientation of the wearable device, a pressure applied to the wearable device, or any combination thereof, wherein the second measure of oxygen saturation is based at least in part on the filtering.

In some examples, a user device may receive a third measure of oxygen saturation associated with the user from a wearable device and based at least in part on a third oxygen saturation measurement performed at a second time, where a duration between the first time and the second time satisfies a threshold. In some examples, the user device may determine an updated oxygen saturation calibration based at least in part on comparing the third measure of oxygen saturation and the second measure of oxygen saturation. In some examples, the user device may calibrate the second measure of oxygen saturation according to the determined updated oxygen saturation calibration.

In some examples, the calibration calculation component 730 may be configured as or otherwise support a means for generating a data structure based at least in part on comparing the first measure of oxygen saturation and the second measure of oxygen saturation, the data structure mapping one or more measures of oxygen saturation to one or more of a position of the wearable device, an orientation of the wearable device, or a pressure applied to the wearable device, wherein determining the oxygen saturation calibration is further based at least in part on the data structure. In some examples, to support determining the oxygen saturation calibration, the calibration calculation component 730 may be configured as or otherwise support a means for determining a difference between the first measure of oxygen saturation and the second measure of oxygen saturation, wherein the oxygen saturation calibration is further based at least in part on the difference.

In some examples, the oxygen saturation calibration is based at least in part on a pulse rate of the user, a signal interference value for the second oxygen saturation measurement, an environmental factor, accelerometer data, pressure data, or any combination thereof. In some examples, the first oxygen saturation measurement corresponds to a first sampling rate and the second oxygen saturation measurement corresponds to a second sampling rate different from the first sampling rate. In some examples, the first anatomical feature of the user, the second anatomical feature of the user, or both may include a finger of the user. In some examples, the wearable device includes a wearable ring device.

Figure 8:
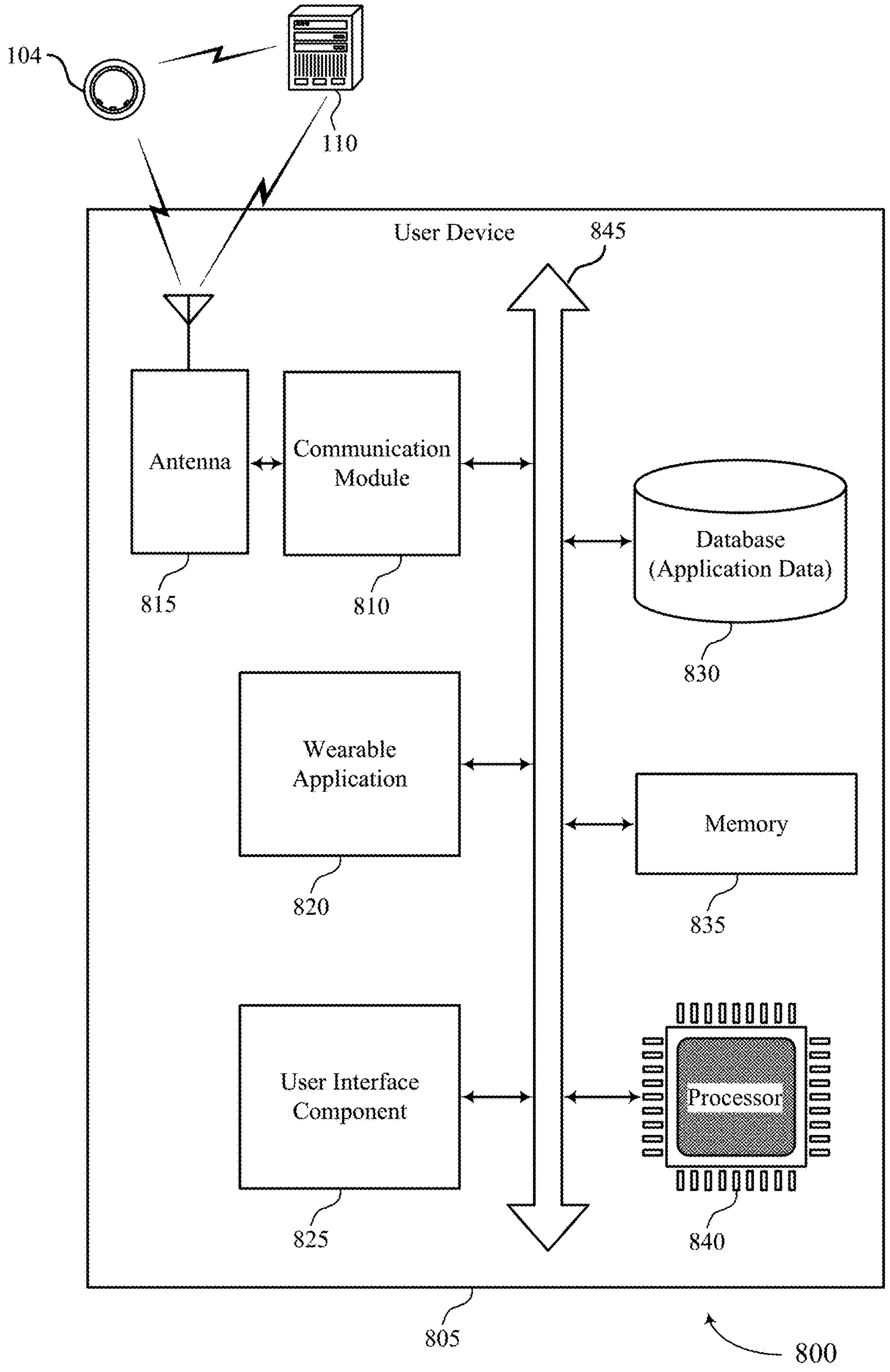
FIG. 8 shows a diagram of a system including a device that supports oxygen saturation calibration in accordance with aspects of the present disclosure.

FIG. 8 shows a diagram of a system 800 including a device 805 that supports oxygen saturation calibration in accordance with aspects of the present disclosure. The device 805 may be an example of or include the components of a device 605 as described herein. The device 805 may include an example of a user device 106, as described previously herein. The device 805 may include components for bi-directional communications including components for transmitting and receiving communications with a wearable device 104 and a server 110, such as a wearable application 820, a communication module 810, an antenna 815, a user interface component 825, a database (application data) 830, a memory 835, and a processor 840. These components may be in electronic communication or otherwise coupled (e.g., operatively, communicatively, functionally, electronically, electrically) via one or more buses (e.g., a bus 845).

The communication module 810 may manage input and output signals for the device 805 via the antenna 815. The communication module 810 may include an example of the communication module 220-*b* of the user device 106 shown and described in FIG. 2. In this regard, the communication module 810 may manage communications with the ring 104 and the server 110, as illustrated in FIG. 2. The communication module 810 may also manage peripherals not integrated into the device 805. In some cases, the communication module 810 may represent a physical connection or port to an external peripheral. In some cases, the communication module 810 may utilize an operating system such as iOS®, ANDROID®, MS-DOS®, MS-WINDOWS®, OS/2®, UNIX®, LINUX®, or another known operating system. In other cases, the communication module 810 may represent or interact with a wearable device (e.g., ring 104), modem, a keyboard, a mouse, a touchscreen, or a similar device. In some cases, the communication module 810 may be implemented as part of the processor 840. In some examples, a user may interact with the device 805 via the communication module 810, user interface component 825, or via hardware components controlled by the communication module 810.

In some cases, the device 805 may include a single antenna 815. However, in some other cases, the device 805 may have more than one antenna 815, which may be capable of concurrently transmitting or receiving multiple wireless transmissions. The communication module 810 may communicate bi-directionally, via the one or more antennas 815, wired, or wireless links as described herein. For example, the communication module 810 may represent a wireless transceiver and may communicate bi-directionally with another wireless transceiver. The communication module 810 may also include a modem to modulate the packets, to provide the modulated packets to one or more antennas 815 for transmission, and to demodulate packets received from the one or more antennas 815.

The user interface component 825 may manage data storage and processing in a database 830. In some cases, a user may interact with the user interface component 825. In other cases, the user interface component 825 may operate automatically without user interaction. The database 830 may be an example of a single database, a distributed database, multiple distributed databases, a data store, a data lake, or an emergency backup database.

The memory 835 may include RAM and ROM. The memory 835 may store computer-readable, computer-executable software including instructions that, when executed, cause the processor 840 to perform various functions described herein. In some cases, the memory 835 may contain, among other things, a BIOS which may control basic hardware or software operation such as the interaction with peripheral components or devices.

The processor 840 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 840 may be configured to operate a memory array using a memory controller. In other cases, a memory controller may be integrated into the processor 840. The processor 840 may be configured to execute computer-readable instructions stored in a memory 835 to perform various functions (e.g., functions or tasks supporting a method and system for sleep staging algorithms).

The wearable application 820 may support performing calibration of a wearable device in accordance with examples as disclosed herein. For example, the wearable application 820 may be configured as or otherwise support a means for receiving, from the wearable device, a first measure of oxygen saturation associated with a user based at least in part on a first oxygen saturation measurement, wherein the first oxygen saturation measurement is performed at a first anatomical feature of the user. The wearable application 820 may be configured as or otherwise support a means for receiving, from the wearable device, a second measure of oxygen saturation associated with the user based at least in part on a second oxygen saturation measurement, wherein the second oxygen saturation measurement is performed at a second anatomical feature of the user. The wearable application 820 may be configured as or otherwise support a means for determining an oxygen saturation calibration based at least in part on comparing the first measure of oxygen saturation and the second measure of oxygen saturation. The wearable application 820 may be configured as or otherwise support a means for calibrating the second measure of oxygen saturation according to the determined oxygen saturation calibration.

By including or configuring the wearable application 820 in accordance with examples as described herein, the device 805 may support techniques for calibrating a wearable device based on multiple SpO2 measurements of a user, which may provide for improved user experience by accounting for variability between positions and orientations at a user.

The wearable application 820 may include an application (e.g., "app"), program, software, or other component which is configured to facilitate communications with a ring 104, server 110, other user devices 106, and the like. For example, the wearable application 820 may include an application executable on a user device 106 which is configured to receive data (e.g., physiological data) from a ring 104, perform processing operations on the received data, transmit and receive data with the servers 110, and cause presentation of data to a user 102.

Figure 9:
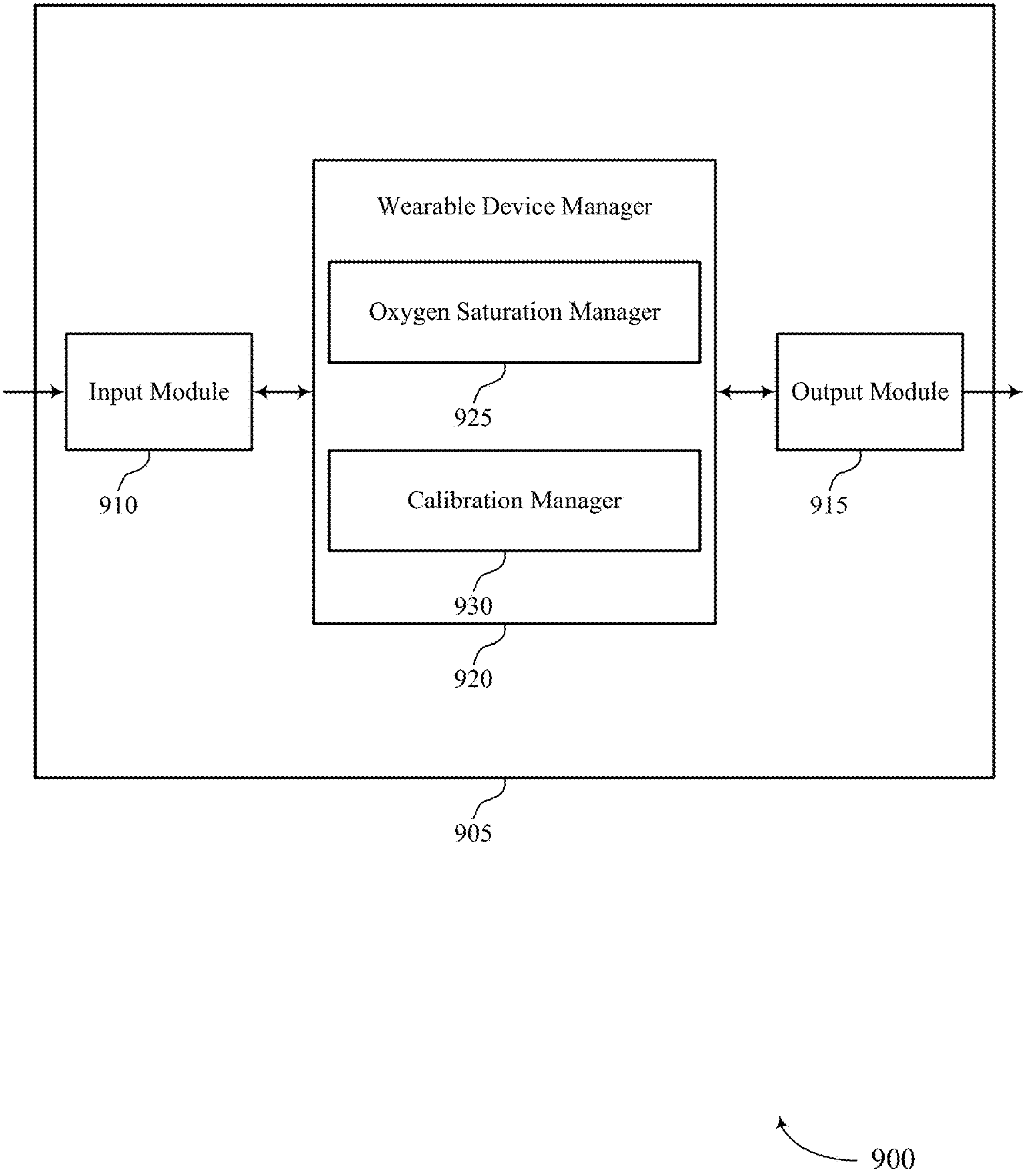
FIG. 9 shows a block diagram of an apparatus that supports oxygen saturation calibration in accordance with aspects of the present disclosure.

FIG. 9 shows a block diagram 900 of a device 905 that supports oxygen saturation calibration in accordance with aspects of the present disclosure. The device 905 may include an input module 910, an output module 915, and a wearable device manager 920. The device 905 may also include a processor. Each of these components may be in communication with one another (e.g., via one or more buses).

For example, the wearable device manager 920 may include an oxygen saturation manager 925 a calibration manager 930, or any combination thereof. In some examples, the wearable device manager 920, or various components thereof, may be configured to perform various operations (e.g., receiving, monitoring, transmitting) using or otherwise in cooperation with the input module 910, the output module 915, or both. For example, the wearable device manager 920 may receive information from the input module 910, send information to the output module 915, or be integrated in combination with the input module 910, the output module 915, or both to receive information, transmit information, or perform various other operations as described herein.

The oxygen saturation manager 925 may be configured as or otherwise support a means for obtaining, at a wearable device, a first measure of oxygen saturation associated with a user based at least in part on performing a first oxygen saturation measurement at a first anatomical feature of the user. The oxygen saturation manager 925 may be configured as or otherwise support a means for obtaining, at the wearable device, a second measure of oxygen saturation associated with the user based at least in part on performing a second oxygen saturation measurement at a second anatomical feature of the user. The calibration manager 930 may be configured as or otherwise support a means for transmitting, to a user device, the first measure of oxygen saturation and the second measure of oxygen saturation.

Figure 10:
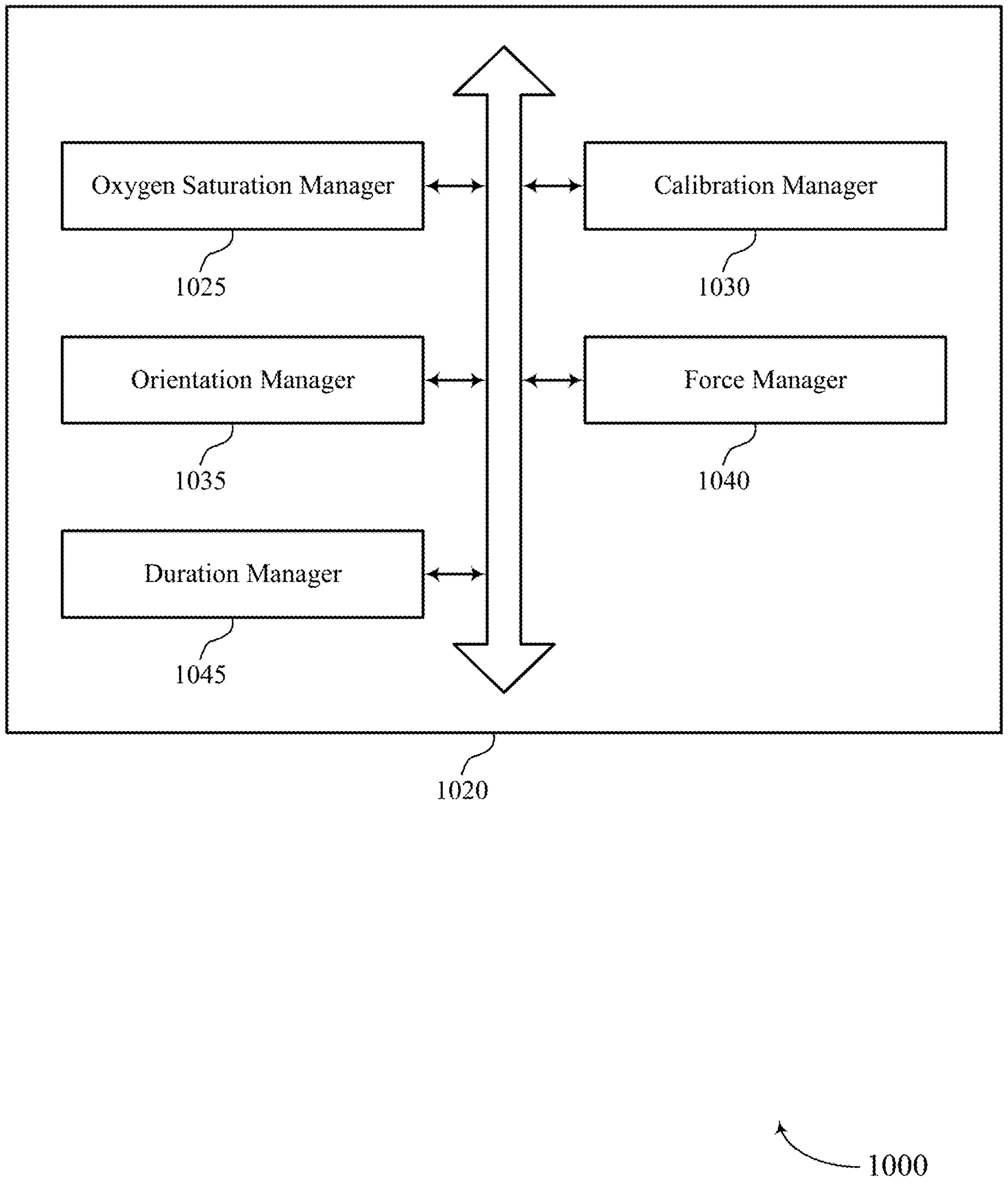
FIG. 10 shows a block diagram of a wearable device manager that supports oxygen saturation calibration in accordance with aspects of the present disclosure.

FIG. 10 shows a block diagram 1000 of a wearable device manager 1020 that supports oxygen saturation calibration in accordance with aspects of the present disclosure. The wearable device manager 1020 may be an example of aspects of a wearable device manager or a wearable device manager 920, or both, as described herein. The wearable device manager 1020, or various components thereof, may be an example of means for performing various aspects of oxygen saturation calibration as described herein. For example, the wearable device manager 1020 may include an oxygen saturation manager 1025, a calibration manager 1030, an orientation manager 1035, a force manager 1040, a duration manager 1045, or any combination thereof. Each of these components may communicate, directly or indirectly, with one another (e.g., via one or more buses).

The oxygen saturation manager 1025 may be configured as or otherwise support a means for obtaining, at a wearable device, a first measure of oxygen saturation associated with a user based at least in part on performing a first oxygen saturation measurement at a first anatomical feature of the user. In some examples, the oxygen saturation manager 1025 may be configured as or otherwise support a means for obtaining, at the wearable device, a second measure of oxygen saturation associated with the user based at least in part on performing a second oxygen saturation measurement at a second anatomical feature of the user. The calibration manager 1030 may be configured as or otherwise support a means for transmitting, to a user device, the first measure of oxygen saturation and the second measure of oxygen saturation.

In some examples, the orientation manager 1035 may be configured as or otherwise support a means for performing the first oxygen saturation measurement in accordance with a set of orientations of the wearable device. In some examples, the set of orientations includes a rotation sequence for the wearable device. In some examples, the force manager 1040 may be configured as or otherwise support a means for performing the first oxygen saturation measurement according to a set of forces applied to an exterior surface of the wearable device, wherein the set of forces corresponds to a change of a distance between the wearable device and the anatomical feature of the user.

In some examples, a wearable device may determine that a duration between the first time and a second time satisfies a threshold. In some examples, the wearable device may obtain, at the wearable device and based at least in part on the determining, a third measure of oxygen saturation associated with the user at the second time based at least in part on performing a third oxygen saturation measurement at the first anatomical feature of the user, the second anatomical feature of the user, or both. In some examples, the wearable device may transmit the third measure of oxygen saturation to the user device.

In some examples, the first oxygen saturation measurement corresponds to a first sampling rate and the second oxygen saturation measurement corresponds to a second sampling rate different from the first sampling rate. In some examples, the first anatomical feature of the user, the second anatomical feature of the user, or both may include a finger of the user. In some examples, the wearable device includes a wearable ring device.

Figure 11:
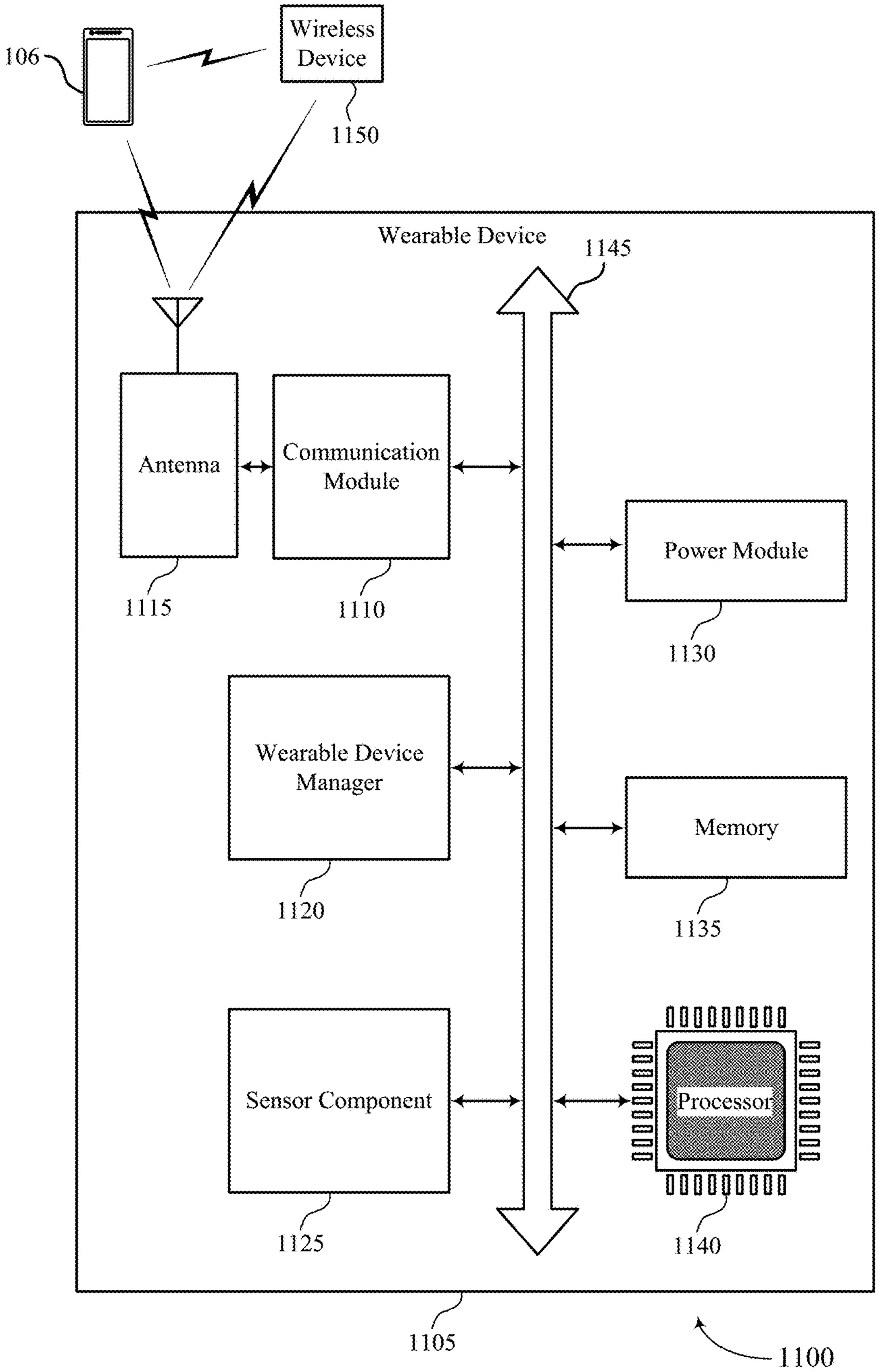
FIG. 11 shows a diagram of a system including a device that supports oxygen saturation calibration in accordance with aspects of the present disclosure.

FIG. 11 shows a diagram of a system 1100 including a device 1105 that supports oxygen saturation calibration in accordance with aspects of the present disclosure. The device 1105 may be an example of or include the components of a device 905 as described herein. The device 1105 may include an example of a wearable device 104, as described previously herein. The device 1105 may include components for bi-directional communications including components for transmitting and receiving communications with a user device 106 and a server 110, such as a wearable device manager 1120, a communication module 1110, an antenna 1115, a sensor component 1125, a power module 1130, a memory 1135, a processor 1140, and a wireless device 1150. These components may be in electronic communication or otherwise coupled (e.g., operatively, communicatively, functionally, electronically, electrically) via one or more buses (e.g., a bus 1145).

For example, the wearable device manager 1120 may be configured as or otherwise support a means for obtaining, at a wearable device, a first measure of oxygen saturation associated with a user based at least in part on performing a first oxygen saturation measurement at a first anatomical feature of the user. The wearable device manager 1120 may be configured as or otherwise support a means for obtaining, at the wearable device, a second measure of oxygen saturation associated with the user based at least in part on performing a second oxygen saturation measurement at a second anatomical feature of the user. The wearable device manager 1120 may be configured as or otherwise support a means for transmitting, to a user device, the first measure of oxygen saturation and the second measure of oxygen saturation.

By including or configuring the wearable device manager 1120 in accordance with examples as described herein, the device 1105 may support techniques for calibrating a wearable device based on multiple SpO2 measurements of a user, which may provide for improved user experience by accounting for variability between positions and orientations at a user.

Figure 12:
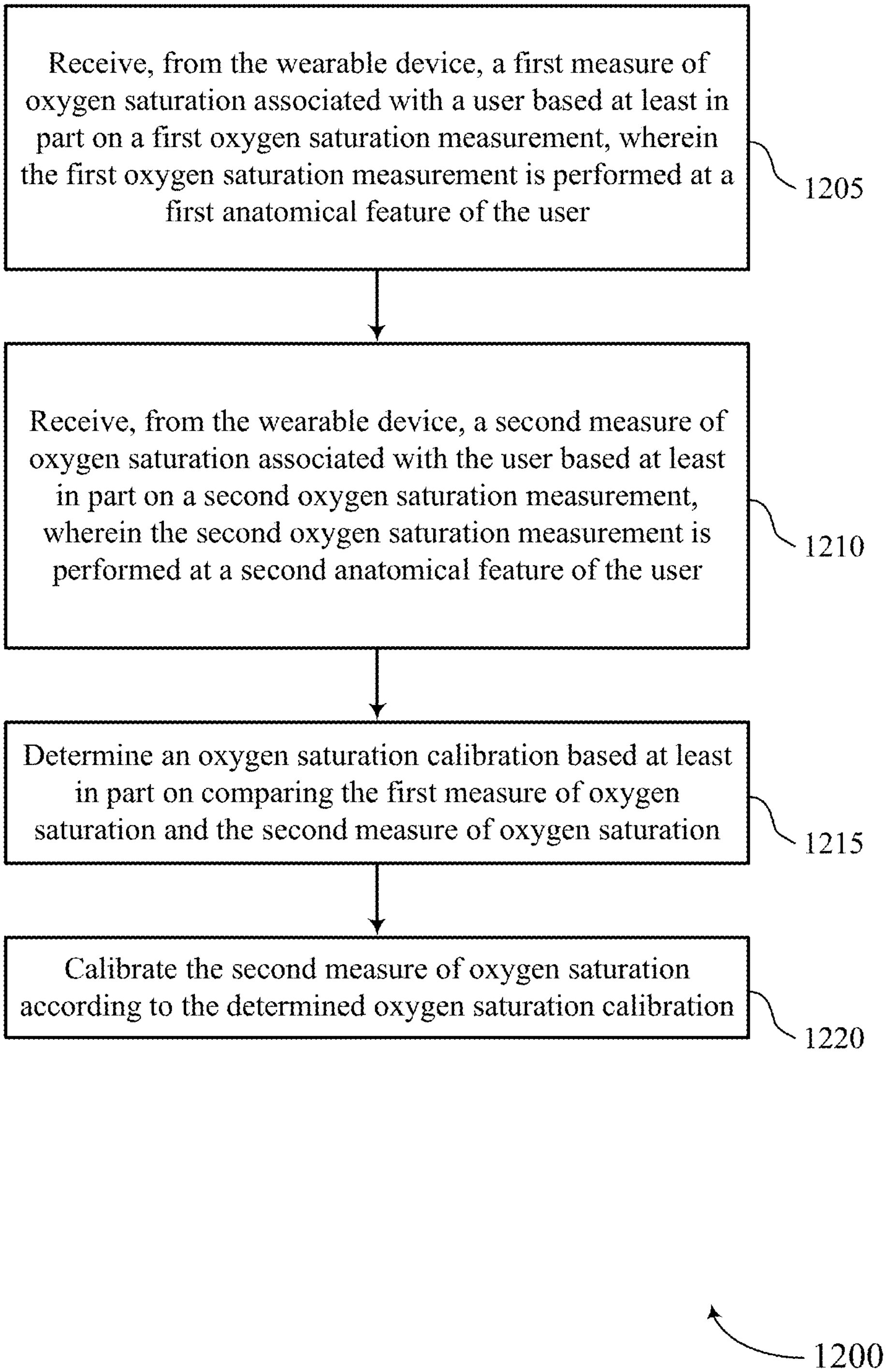
FIGS. 12 through 17 show flowcharts illustrating methods that support oxygen saturation calibration in accordance with aspects of the present disclosure.

FIG. 12 shows a flowchart illustrating a method 1200 that supports oxygen saturation calibration in accordance with aspects of the present disclosure. The operations of the method 1200 may be implemented by a user device or its components as described herein. For example, the operations of the method 1200 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1205, the method may include receiving, from the wearable device, a first measure of oxygen saturation associated with a user based at least in part on a first oxygen saturation measurement, wherein the first oxygen saturation measurement is performed at a first anatomical feature of the user. The operations of 1205 may be performed in accordance with examples as disclosed herein. In some examples, aspects of the operations of 1205 may be performed by an oxygen saturation component 725 as described with reference to FIG. 7.

At 1210, the method may include receiving, from the wearable device, a second measure of oxygen saturation associated with the user based at least in part on a second oxygen saturation measurement, wherein the second oxygen saturation measurement is performed at a second anatomical feature of the user. The operations of 1210 may be performed in accordance with examples as disclosed herein. In some examples, aspects of the operations of 1210 may be performed by an oxygen saturation component 725 as described with reference to FIG. 7.

At 1215, the method may include determining an oxygen saturation calibration based at least in part on comparing the first measure of oxygen saturation and the second measure of oxygen saturation. The operations of 1215 may be performed in accordance with examples as disclosed herein. In some examples, aspects of the operations of 1215 may be performed by a calibration calculation component 730 as described with reference to FIG. 7.

At 1220, the method may include calibrating the second measure of oxygen saturation according to the determined oxygen saturation calibration. The operations of 1220 may be performed in accordance with examples as disclosed herein. In some examples, aspects of the operations of 1220 may be performed by a calibration component 735 as described with reference to FIG. 7.

Figure 13:
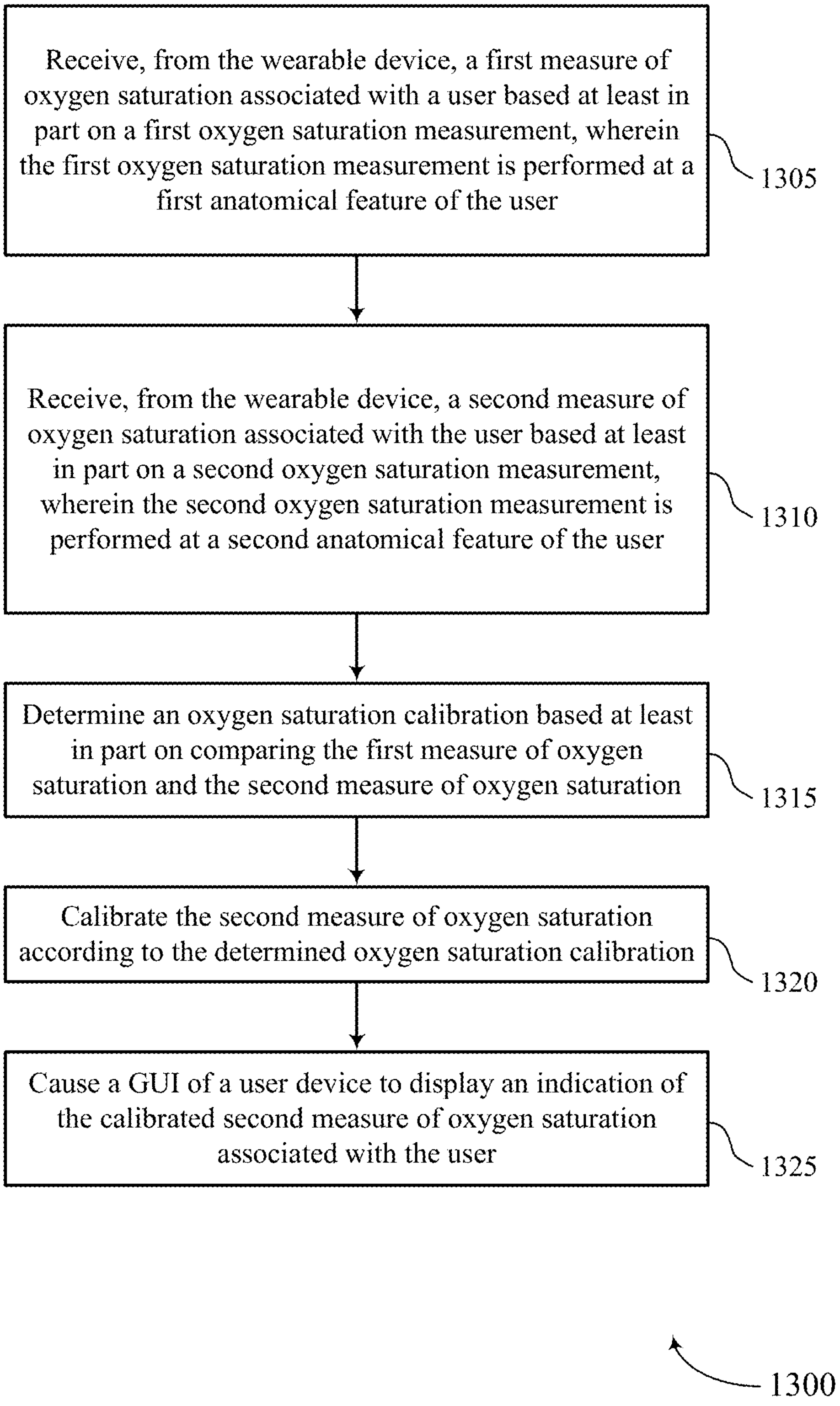

FIG. 13 shows a flowchart illustrating a method 1300 that supports oxygen saturation calibration in accordance with aspects of the present disclosure. The operations of the method 1300 may be implemented by a user device or its components as described herein. For example, the operations of the method 1300 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1305, the method may include receiving, from the wearable device, a first measure of oxygen saturation associated with a user based at least in part on a first oxygen saturation measurement, wherein the first oxygen saturation measurement is performed at a first anatomical feature of the user. The operations of 1305 may be performed in accordance with examples as disclosed herein. In some examples, aspects of the operations of 1305 may be performed by an oxygen saturation component 725 as described with reference to FIG. 7.

At 1310, the method may include receiving, from the wearable device, a second measure of oxygen saturation associated with the user based at least in part on a second oxygen saturation measurement, wherein the second oxygen saturation measurement is performed at a second anatomical feature of the user. The operations of 1310 may be performed in accordance with examples as disclosed herein. In some examples, aspects of the operations of 1310 may be performed by an oxygen saturation component 725 as described with reference to FIG. 7.

At 1315, the method may include determining an oxygen saturation calibration based at least in part on comparing the first measure of oxygen saturation and the second measure of oxygen saturation. The operations of 1315 may be performed in accordance with examples as disclosed herein. In some examples, aspects of the operations of 1315 may be performed by a calibration calculation component 730 as described with reference to FIG. 7.

At 1320, the method may include calibrating the second measure of oxygen saturation according to the determined oxygen saturation calibration. The operations of 1320 may be performed in accordance with examples as disclosed herein. In some examples, aspects of the operations of 1320 may be performed by a calibration component 735 as described with reference to FIG. 7.

At 1325, the method may include causing a GUI of a user device to display an indication of the calibrated second measure of oxygen saturation associated with the user. The operations of 1325 may be performed in accordance with examples as disclosed herein. In some examples, aspects of the operations of 1325 may be performed by a GUI component 740 as described with reference to FIG. 7.

Figure 14:
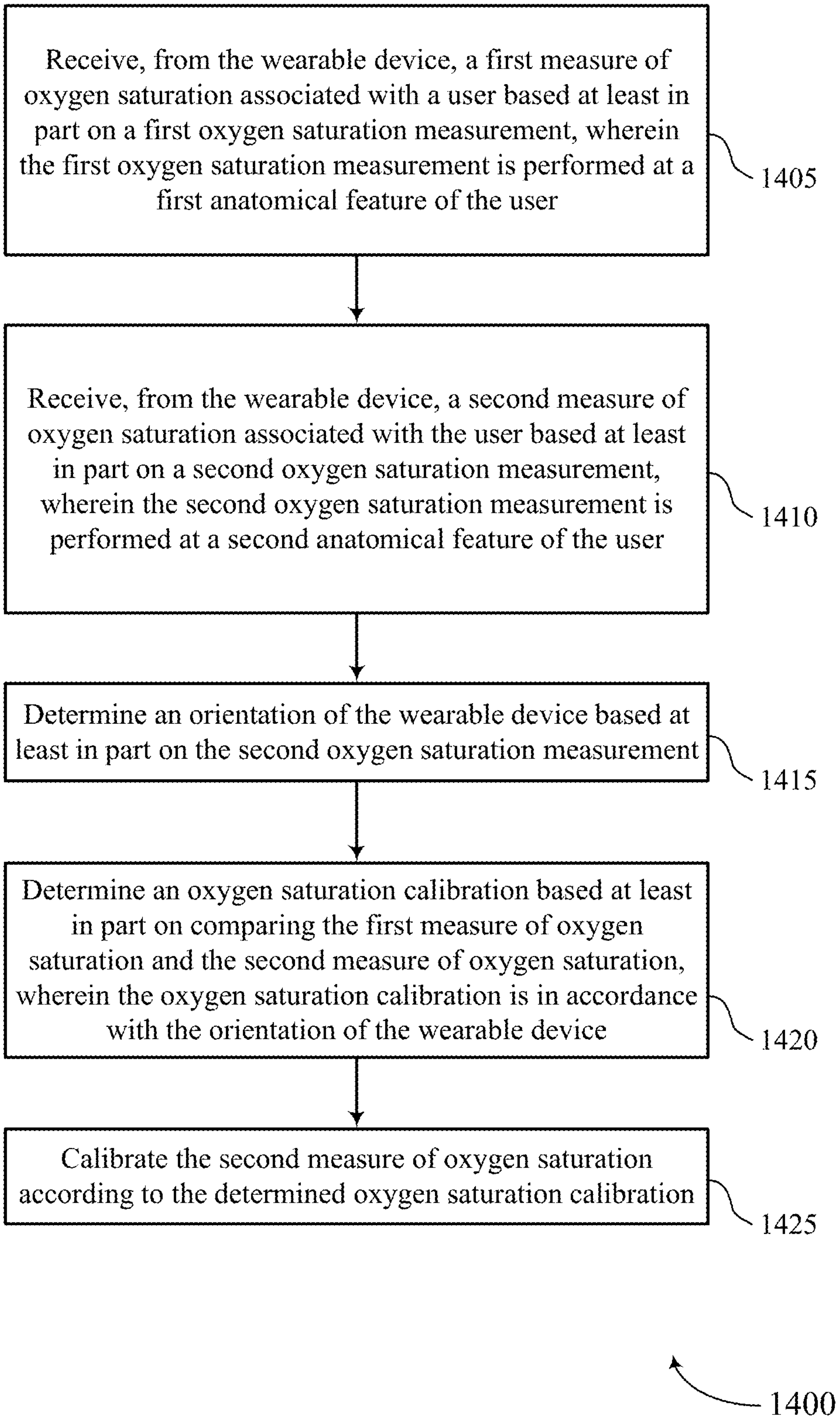

FIG. 14 shows a flowchart illustrating a method 1400 that supports oxygen saturation calibration in accordance with aspects of the present disclosure. The operations of the method 1400 may be implemented by a user device or its components as described herein. For example, the operations of the method 1400 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1405, the method may include receiving, from the wearable device, a first measure of oxygen saturation associated with a user based at least in part on a first oxygen saturation measurement, wherein the first oxygen saturation measurement is performed at a first anatomical feature of the user. The operations of 1405 may be performed in accordance with examples as disclosed herein. In some examples, aspects of the operations of 1405 may be performed by an oxygen saturation component 725 as described with reference to FIG. 7.

At 1410, the method may include receiving, from the wearable device, a second measure of oxygen saturation associated with the user based at least in part on a second oxygen saturation measurement, wherein the second oxygen saturation measurement is performed at a second anatomical feature of the user. The operations of 1410 may be performed in accordance with examples as disclosed herein. In some examples, aspects of the operations of 1410 may be performed by an oxygen saturation component 725 as described with reference to FIG. 7.

At 1415, the method may include determining an orientation of the wearable device based at least in part on the second oxygen saturation measurement. The operations of 1415 may be performed in accordance with examples as disclosed herein. In some examples, aspects of the operations of 1415 may be performed by an orientation component 745 as described with reference to FIG. 7.

At 1420, the method may include determining an oxygen saturation calibration based at least in part on comparing the first measure of oxygen saturation and the second measure of oxygen saturation, wherein the oxygen saturation calibration is in accordance with the orientation of the wearable device. The operations of 1420 may be performed in accordance with examples as disclosed herein. In some examples, aspects of the operations of 1420 may be performed by a calibration calculation component 730 as described with reference to FIG. 7.

At 1425, the method may include calibrating the second measure of oxygen saturation according to the determined oxygen saturation calibration. The operations of 1425 may be performed in accordance with examples as disclosed herein. In some examples, aspects of the operations of 1425 may be performed by a calibration component 735 as described with reference to FIG. 7.

Figure 15:
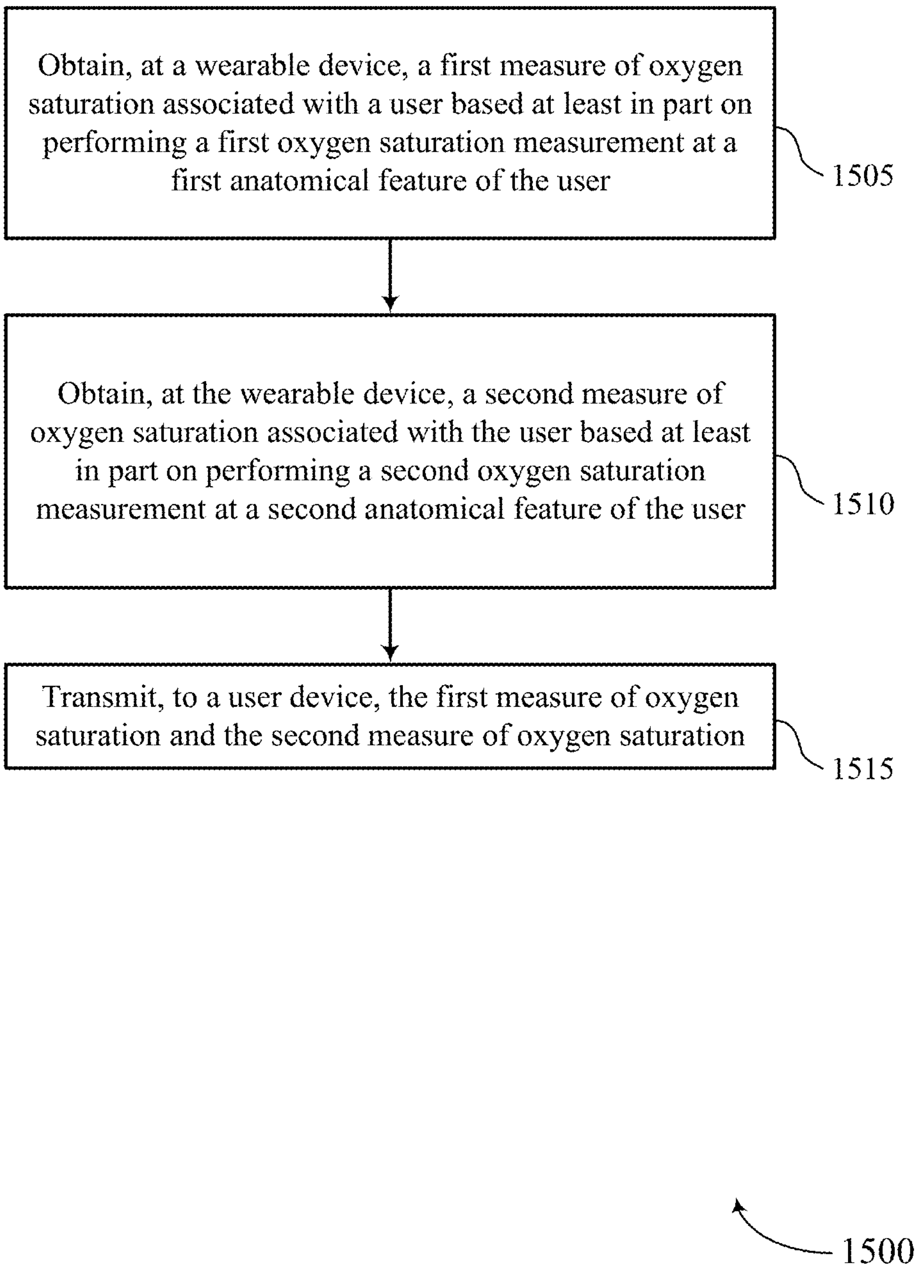

FIG. 15 shows a flowchart illustrating a method 1500 that supports oxygen saturation calibration in accordance with aspects of the present disclosure. The operations of the method 1500 may be implemented by a wearable device or its components as described herein. For example, the operations of the method 1500 may be performed by a wearable device as described with reference to FIGS. 1 through 5 and 9 through 11. In some examples, a wearable device may execute a set of instructions to control the functional elements of the wearable device to perform the described functions. Additionally, or alternatively, the wearable device may perform aspects of the described functions using special-purpose hardware.

At 1505, the method may include obtaining, at a wearable device, a first measure of oxygen saturation associated with a user based at least in part on performing a first oxygen saturation measurement at a first anatomical feature of the user. The operations of 1505 may be performed in accordance with examples as disclosed herein. In some examples, aspects of the operations of 1505 may be performed by an oxygen saturation manager 1025 as described with reference to FIG. 10.

At 1510, the method may include obtaining, at the wearable device, a second measure of oxygen saturation associated with the user based at least in part on performing a second oxygen saturation measurement at a second anatomical feature of the user. The operations of 1510 may be performed in accordance with examples as disclosed herein. In some examples, aspects of the operations of 1510 may be performed by an oxygen saturation manager 1025 as described with reference to FIG. 10.

At 1515, the method may include transmitting, to a user device, the first measure of oxygen saturation and the second measure of oxygen saturation. The operations of 1515 may be performed in accordance with examples as disclosed herein. In some examples, aspects of the operations of 1515 may be performed by a calibration manager 1030 as described with reference to FIG. 10.

Figure 16:
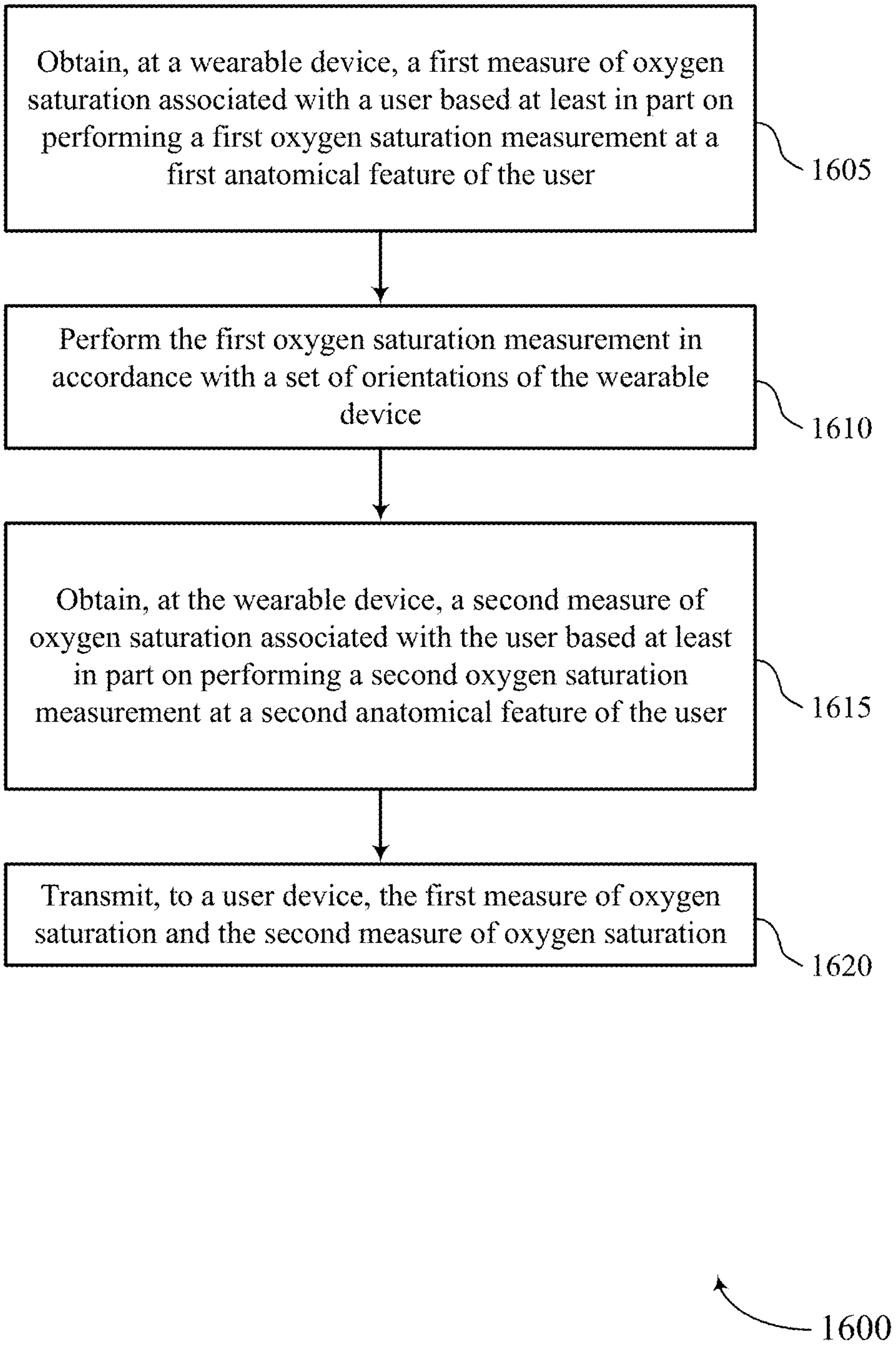

FIG. 16 shows a flowchart illustrating a method 1600 that supports oxygen saturation calibration in accordance with aspects of the present disclosure. The operations of the method 1600 may be implemented by a wearable device or its components as described herein. For example, the operations of the method 1600 may be performed by a wearable device as described with reference to FIGS. 1 through 5 and 9 through 11. In some examples, a wearable device may execute a set of instructions to control the functional elements of the wearable device to perform the described functions. Additionally, or alternatively, the wearable device may perform aspects of the described functions using special-purpose hardware.

At 1605, the method may include obtaining, at a wearable device, a first measure of oxygen saturation associated with a user based at least in part on performing a first oxygen saturation measurement at a first anatomical feature of the user. The operations of 1605 may be performed in accordance with examples as disclosed herein. In some examples, aspects of the operations of 1605 may be performed by an oxygen saturation manager 1025 as described with reference to FIG. 10.

At 1610, the method may include performing the first oxygen saturation measurement in accordance with a set of orientations of the wearable device. The operations of 1610 may be performed in accordance with examples as disclosed herein. In some examples, aspects of the operations of 1610 may be performed by an orientation manager 1035 as described with reference to FIG. 10.

At 1615, the method may include obtaining, at the wearable device, a second measure of oxygen saturation associated with the user based at least in part on performing a second oxygen saturation measurement at a second anatomical feature of the user. The operations of 1615 may be performed in accordance with examples as disclosed herein. In some examples, aspects of the operations of 1615 may be performed by an oxygen saturation manager 1025 as described with reference to FIG. 10.

At 1620, the method may include transmitting, to a user device, the first measure of oxygen saturation and the second measure of oxygen saturation. The operations of 1620 may be performed in accordance with examples as disclosed herein. In some examples, aspects of the operations of 1620 may be performed by a calibration manager 1030 as described with reference to FIG. 10.

Figure 17:
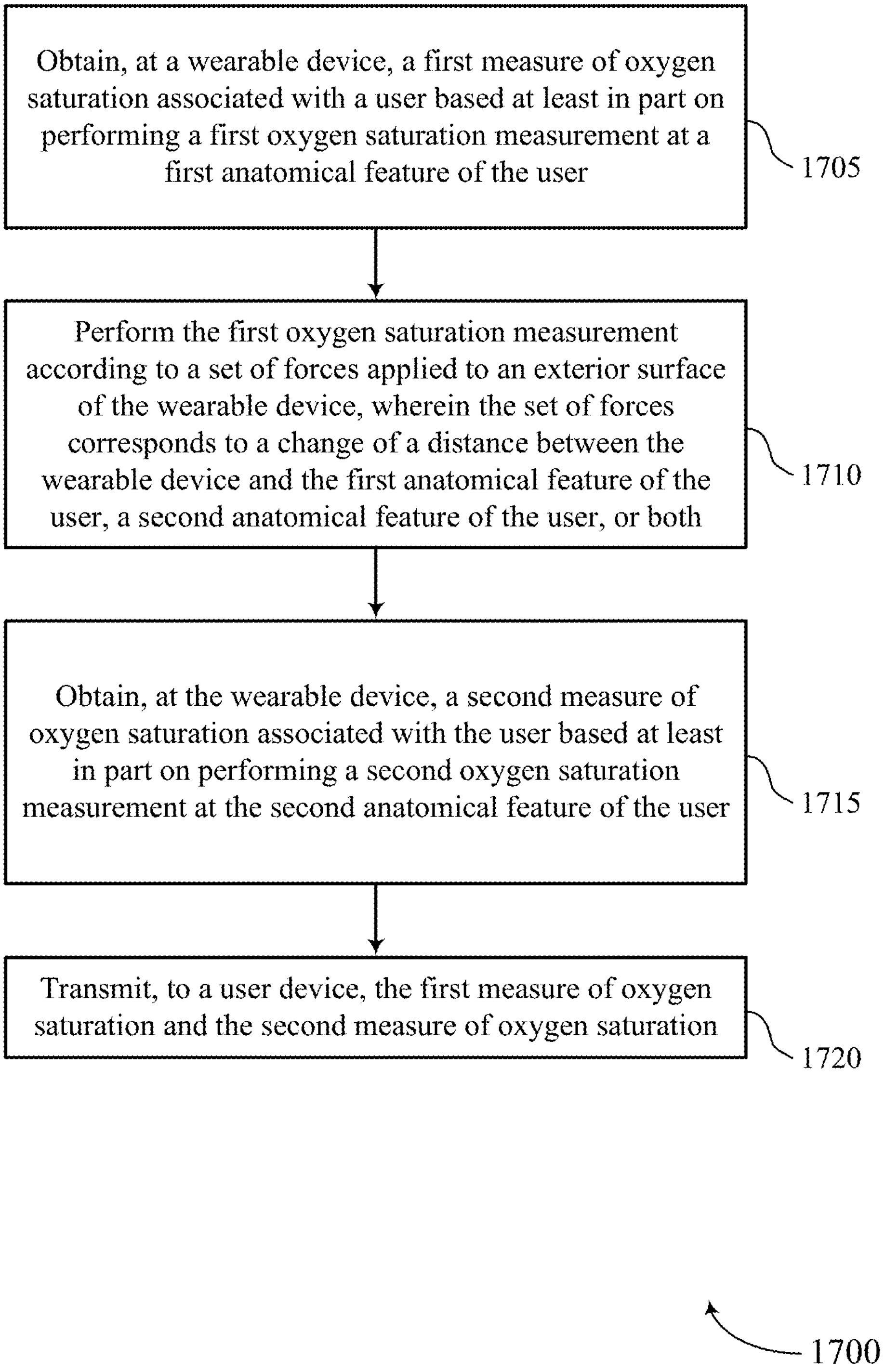

FIG. 17 shows a flowchart illustrating a method 1700 that supports oxygen saturation calibration in accordance with aspects of the present disclosure. The operations of the method 1700 may be implemented by a wearable device or its components as described herein. For example, the operations of the method 1700 may be performed by a wearable device as described with reference to FIGS. 1 through 5 and 9 through 11. In some examples, a wearable device may execute a set of instructions to control the functional elements of the wearable device to perform the described functions. Additionally, or alternatively, the wearable device may perform aspects of the described functions using special-purpose hardware.

At 1705, the method may include obtaining, at a wearable device, a first measure of oxygen saturation associated with a user based at least in part on performing a first oxygen saturation measurement at a first anatomical feature of the user. The operations of 1705 may be performed in accordance with examples as disclosed herein. In some examples, aspects of the operations of 1705 may be performed by an oxygen saturation manager 1025 as described with reference to FIG. 10.

At 1710, the method may include performing the first oxygen saturation measurement according to a set of forces applied to an exterior surface of the wearable device, wherein the set of forces corresponds to a change of a distance between the wearable device and the first anatomical feature of the user, a second anatomical feature of the user, or both. The operations of 1710 may be performed in accordance with examples as disclosed herein. In some examples, aspects of the operations of 1710 may be performed by a force manager 1040 as described with reference to FIG. 10.

At 1715, the method may include obtaining, at the wearable device, a second measure of oxygen saturation associated with the user based at least in part on performing a second oxygen saturation measurement at the second anatomical feature of the user, which may be different from the first anatomical feature of the user. The operations of 1715 may be performed in accordance with examples as disclosed herein. In some examples, aspects of the operations of 1715 may be performed by an oxygen saturation manager 1025 as described with reference to FIG. 10.

At 1720, the method may include transmitting, to a user device, the first measure of oxygen saturation and the second measure of oxygen saturation. The operations of 1720 may be performed in accordance with examples as disclosed herein. In some examples, aspects of the operations of 1720 may be performed by a calibration manager 1030 as described with reference to FIG. 10.

It should be noted that the methods described above describe possible implementations, and that the operations and the steps may be rearranged or otherwise modified and that other implementations are possible. Furthermore, aspects from two or more of the methods may be combined.

A method for performing calibration of a wearable device is described. The method may include receiving, from the wearable device, a first measure of oxygen saturation associated with a user based at least in part on a first oxygen saturation measurement, wherein the first oxygen saturation measurement is performed at a first anatomical feature of the user, receiving, from the wearable device, a second measure of oxygen saturation associated with the user based at least in part on a second oxygen saturation measurement, wherein the second oxygen saturation measurement is performed at a second anatomical feature of the user, determining an oxygen saturation calibration based at least in part on comparing the first measure of oxygen saturation and the second measure of oxygen saturation, and calibrating the second measure of oxygen saturation according to the determined oxygen saturation calibration.

An apparatus for performing calibration of a wearable device is described. The apparatus may include a processor, memory coupled with the processor, and instructions stored in the memory. The instructions may be executable by the processor to cause the apparatus to receive, from the wearable device, a first measure of oxygen saturation associated with a user based at least in part on a first oxygen saturation measurement, wherein the first oxygen saturation measurement is performed at a first anatomical feature of the user, receive, from the wearable device, a second measure of oxygen saturation associated with the user based at least in part on a second oxygen saturation measurement, wherein the second oxygen saturation measurement is performed at a second anatomical feature of the user, determine an oxygen saturation calibration based at least in part on comparing the first measure of oxygen saturation and the second measure of oxygen saturation, and calibrate the second measure of oxygen saturation according to the determined oxygen saturation calibration.

Another apparatus for performing calibration of a wearable device is described. The apparatus may include means for receiving, from the wearable device, a first measure of oxygen saturation associated with a user based at least in part on a first oxygen saturation measurement, wherein the first oxygen saturation measurement is performed at a first anatomical feature of the user, means for receiving, from the wearable device, a second measure of oxygen saturation associated with the user based at least in part on a second oxygen saturation measurement, wherein the second oxygen saturation measurement is performed at a second anatomical feature of the user, means for determining an oxygen saturation calibration based at least in part on comparing the first measure of oxygen saturation and the second measure of oxygen saturation, and means for calibrating the second measure of oxygen saturation according to the determined oxygen saturation calibration.

A non-transitory computer-readable medium storing code for performing calibration of a wearable device is described. The code may include instructions executable by a processor to receive, from the wearable device, a first measure of oxygen saturation associated with a user based at least in part on a first oxygen saturation measurement, wherein the first oxygen saturation measurement is performed at a first anatomical feature of the user, receive, from the wearable device, a second measure of oxygen saturation associated with the user based at least in part on a second oxygen saturation measurement, wherein the second oxygen saturation measurement is performed at a second anatomical feature of the user, determine an oxygen saturation calibration based at least in part on comparing the first measure of oxygen saturation and the second measure of oxygen saturation, and calibrate the second measure of oxygen saturation according to the determined oxygen saturation calibration.

Some examples of the method, apparatuses, and non-transitory computer-readable medium described herein may further include operations, features, means, or instructions for causing a GUI of a user device to display an indication of the calibrated second measure of oxygen saturation associated with the user.

Some examples of the method, apparatuses, and non-transitory computer-readable medium described herein may further include operations, features, means, or instructions for determining an orientation of the wearable device based at least in part on the second oxygen saturation measurement, wherein the oxygen saturation calibration may be in accordance with the orientation of the wearable device.

In some examples of the method, apparatuses, and non-transitory computer-readable medium described herein, the set of orientations comprises a rotation sequence for the wearable device.

In some examples, the first anatomical feature and the second anatomical feature may be associated with different localities of a same human body part of the user. In some other examples, the first anatomical feature may be associated with a first human body part of the user and the second anatomical feature may be associated with a second human body part of the user.

Some examples of the method, apparatuses, and non-transitory computer-readable medium described herein may further include operations, features, means, or instructions for determining a force applied to the exterior surface of the wearable device based at least in part on the second oxygen saturation measurement, wherein the oxygen saturation calibration may be in accordance with the force.

In some examples of the method, apparatuses, and non-transitory computer-readable medium described herein, calibrating the second measure of oxygen saturation may include operations, features, means, or instructions for filtering the second oxygen saturation measurement based at least in part on a position of the wearable device, an orientation of the wearable device, a pressure applied to the wearable device, or any combination thereof, wherein the second measure of oxygen saturation may be based at least in part on the filtering.

Some examples of the method, apparatuses, and non-transitory computer-readable medium described herein may further include operations, features, means, or instructions for receiving, from the wearable device, a third measure of oxygen saturation associated with the user based at least in part on a third oxygen saturation measurement performed at a second time, wherein a duration between the first time and the second time satisfies a threshold, determining an updated oxygen saturation calibration based at least in part on comparing the third measure of oxygen saturation and the second measure of oxygen saturation, and calibrating the second measure of oxygen saturation according to the determined updated oxygen saturation calibration.

Some examples of the method, apparatuses, and non-transitory computer-readable medium described herein may further include operations, features, means, or instructions for generating a data structure based at least in part on comparing the first measure of oxygen saturation and the second measure of oxygen saturation, the data structure mapping one or more measures of oxygen saturation to one or more of a position of the wearable device, an orientation of the wearable device, or a pressure applied to the wearable device, wherein determining the oxygen saturation calibration may be further based at least in part on the data structure.

In some examples of the method, apparatuses, and non-transitory computer-readable medium described herein, determining the oxygen saturation calibration may include operations, features, means, or instructions for determining a difference between the first measure of oxygen saturation and the second measure of oxygen saturation, wherein the oxygen saturation calibration may be further based at least in part on the difference.

In some examples of the method, apparatuses, and non-transitory computer-readable medium described herein, the oxygen saturation calibration may be based at least in part on a pulse rate of the user, a signal interference value for the second oxygen saturation measurement, an environmental factor, accelerometer data, pressure data, or any combination thereof.

In some examples of the method, apparatuses, and non-transitory computer-readable medium described herein, the first oxygen saturation measurement corresponds to a first sampling rate and the second oxygen saturation measurement corresponds to a second sampling rate different from the first sampling rate.

In some examples of the method, apparatuses, and non-transitory computer-readable medium described herein, the first anatomical feature of the user, the second anatomical feature of the user, or both comprises a finger of the user.

In some examples of the method, apparatuses, and non-transitory computer-readable medium described herein, the wearable device comprises a wearable ring device.

A method is described. The method may include obtaining, at a wearable device, a first measure of oxygen saturation associated with a user based at least in part on performing a first oxygen saturation measurement at a first anatomical feature of the user, obtaining, at the wearable device, a second measure of oxygen saturation associated with the user based at least in part on performing a second oxygen saturation measurement at a second anatomical feature of the user, and transmitting, to a user device, the first measure of oxygen saturation and the second measure of oxygen saturation.

An apparatus is described. The apparatus may include a processor, memory coupled with the processor, and instructions stored in the memory. The instructions may be executable by the processor to cause the apparatus to obtain, at a wearable device, a first measure of oxygen saturation associated with a user based at least in part on performing a first oxygen saturation measurement at a first anatomical feature of the user, obtain, at the wearable device, a second measure of oxygen saturation associated with the user based at least in part on performing a second oxygen saturation measurement at a second anatomical feature of the user, and transmit, to a user device, the first measure of oxygen saturation and the second measure of oxygen saturation.

Another apparatus is described. The apparatus may include means for obtaining, at a wearable device, a first measure of oxygen saturation associated with a user based at least in part on performing a first oxygen saturation measurement at a first anatomical feature of the user, means for obtaining, at the wearable device, a second measure of oxygen saturation associated with the user based at least in part on performing a second oxygen saturation measurement at a second anatomical feature of the user, and means for transmitting, to a user device, the first measure of oxygen saturation and the second measure of oxygen saturation.

A non-transitory computer-readable medium storing code is described. The code may include instructions executable by a processor to obtain, at a wearable device, a first measure of oxygen saturation associated with a user based at least in part on performing a first oxygen saturation measurement at a first anatomical feature of the user, obtain, at the wearable device, a second measure of oxygen saturation associated with the user based at least in part on performing a second oxygen saturation measurement at a second anatomical feature of the user, and transmit, to a user device, the first measure of oxygen saturation and the second measure of oxygen saturation.

Some examples of the method, apparatuses, and non-transitory computer-readable medium described herein may further include operations, features, means, or instructions for performing the first oxygen saturation measurement in accordance with a set of orientations of the wearable device.

In some examples of the method, apparatuses, and non-transitory computer-readable medium described herein, the set of orientations comprises a rotation sequence for the wearable device.

Some examples of the method, apparatuses, and non-transitory computer-readable medium described herein may further include operations, features, means, or instructions for performing the first oxygen saturation measurement according to a set of forces applied to an exterior surface of the wearable device, wherein the set of forces corresponds to a change of a distance between the wearable device and the first anatomical feature of the user, the second anatomical feature of the user, or both.

Some examples of the method, apparatuses, and non-transitory computer-readable medium described herein may further include operations, features, means, or instructions for determining that a duration between the first time and a second time satisfies a threshold, obtaining, at the wearable device and based at least in part on the determining, a third measure of oxygen saturation associated with the user at the second time based at least in part on performing a third oxygen saturation measurement at the first anatomical feature of the user, and transmitting, to the user device, the third measure of oxygen saturation.

In some examples of the method, apparatuses, and non-transitory computer-readable medium described herein, the first oxygen saturation measurement corresponds to a first sampling rate and the second oxygen saturation measurement corresponds to a second sampling rate different from the first sampling rate.

In some examples of the method, apparatuses, and non-transitory computer-readable medium described herein, the first anatomical feature of the user, the second anatomical feature of the user, or both comprises a finger of the user.

In some examples of the method, apparatuses, and non-transitory computer-readable medium described herein, the wearable device comprises a wearable ring device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for performing calibration of a wearable device, comprising:

receiving, from the wearable device, a first measure of oxygen saturation associated with a user based at least in part on a first oxygen saturation measurement, wherein the first oxygen saturation measurement is performed at a first locality of a first anatomical feature of the user;

receiving, from the wearable device, a second measure of oxygen saturation associated with the user based at least in part on a second oxygen saturation measurement, wherein the second oxygen saturation measurement is performed at a second locality of a second anatomical feature of the user, wherein the first locality and the second locality are different localities;

determining an oxygen saturation calibration value, based at least in part on comparing the first measure of oxygen saturation and the second measure of oxygen saturation; and calibrating the second measure of oxygen saturation according to the oxygen saturation calibration value, wherein calibrating the second measure of oxygen saturation comprises applying the oxygen saturation calibration value to adjust the second measure of oxygen saturation.

2. The method of claim 1, further comprising:

causing a graphical user interface of a user device to display an indication of the calibrated second measure of oxygen saturation associated with the user.

3. The method of claim 1, wherein the first oxygen saturation measurement is performed according to a set of orientations of the wearable device, the method comprising:

determining an orientation of the wearable device based at least in part on the second oxygen saturation measurement, wherein the oxygen saturation calibration value is in accordance with the orientation of the wearable device.

4. The method of claim 3, wherein the set of orientations comprises a rotation sequence for the wearable device.

5. The method of claim 1, wherein the first oxygen saturation measurement is performed according to a set of forces applied to an exterior surface of the wearable device, the set of forces changing a first distance between the wearable device and the first anatomical feature of the user, a second distance between the wearable device and the second anatomical feature of the user, or both, the method comprising:

determining a force applied to the exterior surface of the wearable device based at least in part on the second oxygen saturation measurement, wherein the oxygen saturation calibration value is in accordance with the force.

6. The method of claim 1, wherein calibrating the second measure of oxygen saturation comprises:

filtering the second oxygen saturation measurement based at least in part on a position of the wearable device, an orientation of the wearable device, a pressure applied to the wearable device, or any combination thereof, wherein the second measure of oxygen saturation is based at least in part on the filtering.

7. The method of claim 1, wherein the first measure of oxygen saturation is received at a first time, the method comprising:

receiving, from the wearable device, a third measure of oxygen saturation associated with the user based at least in part on a third oxygen saturation measurement performed at a second time, wherein a duration between the first time and the second time satisfies a threshold;

determining an updated oxygen saturation calibration value based at least in part on comparing the third measure of oxygen saturation and the second measure of oxygen saturation; and calibrating the second measure of oxygen saturation according to the updated oxygen saturation calibration value.

8. The method of claim 1, further comprising:

generating a data structure based at least in part on comparing the first measure of oxygen saturation and the second measure of oxygen saturation, the data structure mapping one or more measures of oxygen saturation to one or more of a position of the wearable device, an orientation of the wearable device, or a pressure applied to the wearable device, wherein determining the oxygen saturation calibration value is further based at least in part on the data structure.

9. The method of claim 1, wherein determining the oxygen saturation calibration value comprises:

determining a difference between the first measure of oxygen saturation and the second measure of oxygen saturation, wherein the oxygen saturation calibration value is further based at least in part on the difference.

10. The method of claim 1, wherein the oxygen saturation calibration value is based at least in part on a pulse rate of the user, a signal interference value for the second oxygen saturation measurement, an environmental factor, accelerometer data, pressure data, or any combination thereof.

11. The method of claim 1, wherein the first oxygen saturation measurement corresponds to a first sampling rate and the second oxygen saturation measurement corresponds to a second sampling rate different from the first sampling rate.

12. The method of claim 1, wherein the first anatomical feature and the second anatomical feature are a same human body part of the user.

13. The method of claim 1, wherein the first anatomical feature is a first human body part of the user and the second anatomical feature is a second human body part of the user that is different from the first human body part.

14. The method of claim 1, wherein the wearable device comprises a wearable ring device.

* * * * *